US006328962B2

(12) United States Patent
Anand et al.

(10) Patent No.: US 6,328,962 B2
(45) Date of Patent: Dec. 11, 2001

(54) METHOD FOR DELIVERY OF ANTIGENS TO SELECTED CELLS OF THE IMMUNE SYSTEM USING CHIMERIC ANTIBODIES

(75) Inventors: Naveen N. Anand, Downsview; Brian H. Barber, Mississauga; George A. Cates, Richmond Hill; Judith E. Caterini, Ajax; Michel H. Klein, Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 08/973,518

(22) PCT Filed: Jun. 7, 1996

(86) PCT No.: PCT/CA96/00400

§ 371 Date: Apr. 7, 1998

§ 102(e) Date: Apr. 7, 1998

(87) PCT Pub. No.: WO96/40941

PCT Pub. Date: Dec. 19, 1996

Related U.S. Application Data

(63) Continuation of application No. 08/483,576, filed on Jun. 7, 1995, now abandoned.

(51) Int. Cl.[7] ........................ A61K 39/44; A61K 39/395; A61K 38/00

(52) U.S. Cl. ........................................... 424/134.1; 514/21

(58) Field of Search ............................. 424/134.1; 514/21

(56) References Cited

U.S. PATENT DOCUMENTS

| | | | | |
|---|---|---|---|---|
| 4,950,480 | * | 8/1990 | Barber | 424/85.5 |
| 5,194,254 | * | 3/1993 | Barber | 424/85.5 |
| 5,196,320 | | 3/1993 | Gillies et al. . | |

FOREIGN PATENT DOCUMENTS

| | | |
|---|---|---|
| 0 481 790 A | 4/1992 | (EP) . |
| WO 94/06469 | 3/1994 | (WO) . |
| WO 94/29389 | 12/1994 | (WO) . |

OTHER PUBLICATIONS

Cook J. et al Vaccine, vol. 13, No. 18, Dec. 1995, pp. 1770–1778.

Carayanniotis, G. et al; Nature (Lond) (1987) 327:59–61.

Carayanniotis, G. et al; Mol Immunol. (1988) 25:907–911.

"Molecular Cloning: A Laboratory Manual", ed. Sambrook, J.; Fritsch, E. F. and Maniatis T; (1989) Cold Spring Harbour Laboratory Press.

Kozak M.; Cell, (1986), 44:283–288.

Ulmer et al. 1993. Curre. Opinion. Invest. Drugs 2: 983–989.

Zaghouani, H. et al, Proceedings of the Nat. Acad. Of Sciences of the USA—vol. 92/No. 2/Jan. 17, 1995. pp 631–635.

Baier et al. (Apr. 1995) J. Virol. vol. 69(4):2357–65.

* cited by examiner

*Primary Examiner*—David Saunders
*Assistant Examiner*—Mary Beth Tung
(74) *Attorney, Agent, or Firm*—Sim & McBurney

(57) ABSTRACT

Antibody molecules specific for surface structures of antigen presenting cells that have been modified to include an antigen moiety at a specific site therein to produce novel conjugate antibody molecules are disclosed. These conjugate molecules are produced by genetic modification of genes encoding light and heavy chains of the surface structure specific antibody, and expression in mammalian cells to produce the conjugate antibody. The conjugate antibody retained specificity for antigen presenting cells and contained the antigen moiety. The conjugate antibody molecules deliver the antigen to antigen presenting cells to produce an enhanced immune response to a host immunized therewith. The conjugate antibody molecules and nucleic acid molecules encoding them are useful as antigens and as immunogens in diagnostic and prophylactic applications.

11 Claims, 17 Drawing Sheets

FIG.1A $V_L$ sequence of the light chain of murine 44H104 mab:

ATG GAC ATG AGG GTT CCT GCT CAC GTT TTT GGC TTC TTG TTG CTC TGG TTT
MET Asp MET Arg Val Pro Ala His Val Phe Gly Phe Leu Leu Leu Trp Phe

CCA GGT ACC AGA TGT GAC ATC CAG ATG ACC CAG TCT CCA TCC TCC TTA TCT
Pro Gly Thr Arg Cys Asp Ile Gln MET Thr Gln Ser Pro Ser Ser Leu Ser

GCC TCT CTG GGA CAA AGA GTC AGT CTC ACT TGT CGG GCA AGT CAG GAA ATT
Ala Ser Leu Gly Gln Arg Val Ser Leu Thr Cys Arg Ala Ser Gln Glu Ile

AGT GGT TAC TTA ACC TGG CTT CAG CAG AAA CCA GAT GGA ACT ATT AAA CGC
Ser Gly Tyr Leu Thr Trp Leu Gln Gln Lys Pro Asp Gly Thr Ile Lys Arg

CTG GTC TAC GCC GCG TCC ACT TTA GAT TCT GGT GTC CCA AAA AGG TTC AGT
Leu Val Tyr Ala Ala Ser Thr Leu Asp Ser Gly Val Pro Lys Arg Phe Ser

GGC AGT AGG TCT GGG TCA GAT TAT TCT CTC ACC ATC AGC AGC CTT GAG TCT
Gly Ser Arg Ser Gly Ser Asp Tyr Ser Leu Thr Ile Ser Ser leu Glu Ser GAA GAT TTT GCA GAC TAT TAC TGT CTA CAA TAT ACT AAT TAT CCG CTC ACG
Glu Asp Phe Ala Asp Tyr Tyr Cys Leu Gln Tyr Thr Asp Tyr Pro Leu Thr TTC GGT GCT GGG ACC AAG CTG GAG CTG AAA
Phe Gly Ala Gly Thr Lys Leu Glu Leu Lys

FIG.1B $V_H$ sequence of the heavy chain of murine 44H104 mab:

ATG GCT CTC CTG GTA CTG TTC CTC TCC CTG GCT GCA TTT CCA AGC TGT GGT
MET Ala Leu Leu Val Leu Phe Leu Ser Leu Ala Ala Phe Pro Ser Cys Gly

GTC CTG TCC CAG GTG CAG CTG AAG GAG TCA GGA CCT GGC CTG GTG GCG CCC
Val Leu Ser Gln Val Gln Leu Lys Glu Ser Gly Pro Gly Leu Val Ala Pro

TCA CAG AGC CTG TCC ATC ACT TGC ACT GTC TCT GGG TTT TCA TTA ACC AGC
Ser Gln Ser Leu Ser Ile Thr Cys Thr Val Ser Gly Phe Ser Leu Thr Ser

TAT GGT GTA CAC TGG GTT CGC CAG CCT CCA GGA AAG GGT CTG GAG TGG CTG
Tyr Gly Val His Trp Val Arg Gln Pro Pro Gly Lys Gly Leu Glu Trp Leu

GGA GTA ATA TGG GCT GGT GGA AGC ATA AAT TAT AAT TCG GCT CTC ATG TCC
Gly Val Ser Trp Ala Gly Gly Ser Ile Asn Tyr Asn Ser Ala Leu MET Ser

AGA CTG AGC ATC AGC AAA GAC AAC TTC AAG AGC CAA GTT TTC TTA AAA ATG
Arg Leu Ser Ile Ser Lys Asp Asn Phe Lys Ser Gln Val Phe Leu Lys MET

AGC AGT CTG CAA ACT GAT GAC ACA GCC ATG TAC TAC TGT GCC AGA GCC TAT
Ser Ser Leu Gln Thr Asp Asp Thr Ala MET Tyr Tyr Cys Ala Arg Ala Tyr

GGT GAC TAC GTC CAC TAT GCT ATG GAC TAC TGG GGT CAA GGA ACC TCA GTC
Gly Asp Tyr Val His Tyr Ala MET Asp Tyr Trp Gly Gln Gly Thr Ser Val

ACC GCC TCC TCA
Thr Ala Ser Ser

Assembly of gene encoding CLTB36

Amino acid seq. GPKEPFRDYVDRFYK NKRKRIHIGPGRAFYTTKN

Gene seq. GGTCTAAAGAACCTTTTAGAGACTATGTTGATAGGTTTTA
TAAGAATAAGAGGAAGAGGATACATATAGGGCCTGGT
AGGGCTTTTTATACTACTAAGAATTAATAA

| | |
|---|---|
| CLTB36.1 | CATTATGGATCCGGTCCTAAAGAACCTTTTAGAGACTATGTTGAT AGGTTTTATAAGAAT |
| CLTB36.2 | GCCCTACCAGGCCCTATATGTATCCTCTTCCTCTTATTCTTATAAA ACCTA |
| CLTB36.3 | AGGGCCTGGTAGGGCTTTTTATACTACTAAGAATTAATAAAAGCT TTAGCG |

Pr LC.F CATTATGGATCCGGTCCTAA (*BamH I*: GGATCC)

Pr HC.F GTCAGGTACCGGTCCTAAAGAACCTTTTAG (*Kpn I*: GGTACC)

Pr R GGCTAAAGCTTTTATTAATTC (*Hind III*: AAGCTT)

FIG.2C

Assembly of chimeric 44H104-CLTB36 light chain gene

*Hind III*
Pr. 1 AGCCTAAGCTTCCGCCATGGACATGAGGGTTCCTGCTC

*Xho I*
Pr. 2 CCGTTTCAGCTCGAGCTTGGTCCCAGCACCGAA

*Xho I*
Pr. 3 CCTACTCGAGCTGAAACGGACTGTGGCTGCACCATCTGTC

*BamH I*
Pr. 4 ATTAAAGCTTTTACTAGGATCCACACTCTCCCCTGTTGAAGCTC

FIG.3B.

```
          Hind III
Pr. 5 AGCTAAGCTTCCGCCATGGCTCTCCTGGTACTGTTC
          Spe I
Pr. 6 GCGCACTAGTTCCTTGACCCCAGTAGTCC
          Spe I
Pr. 7 GCGCACTAGTGTCACCGCCTCCTCAGCCTCCACCAAGGGCCCATCGGTCTTC
          Hind III
Pr. 8 ACGCAAGCTTTTACTAGGTACCTTTACCCGGAGACAGGGAGAG
```

FIG.4B.

Epitope Recognition on Recombinant $H^+L^+$ Human Chimeric Antibody Bound to HLA-DR Anti-Human IgG Epitope Recognition on Recombinant H+L+ Human Chimeric Antibody Bound to HLA-DR Anti-CLTB-36

FIG. 9A - Non-Reduced
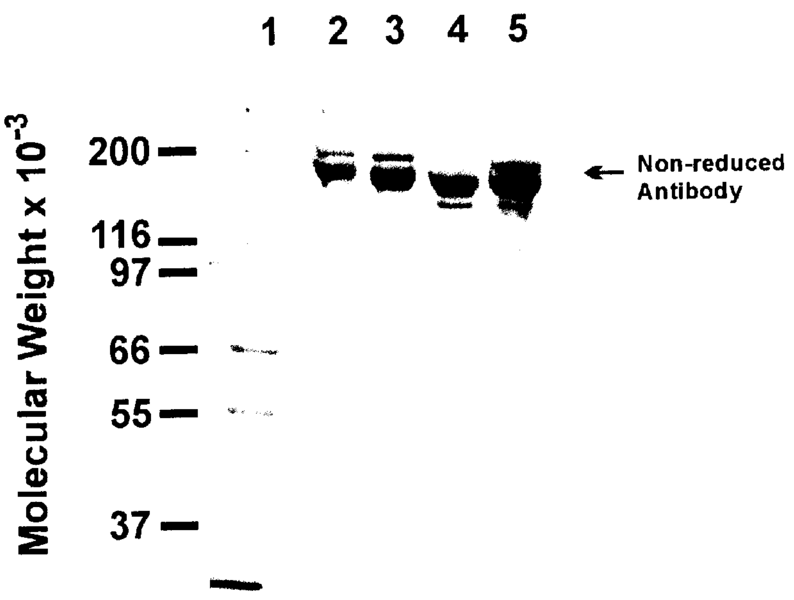
FIG. 9B - Reduced
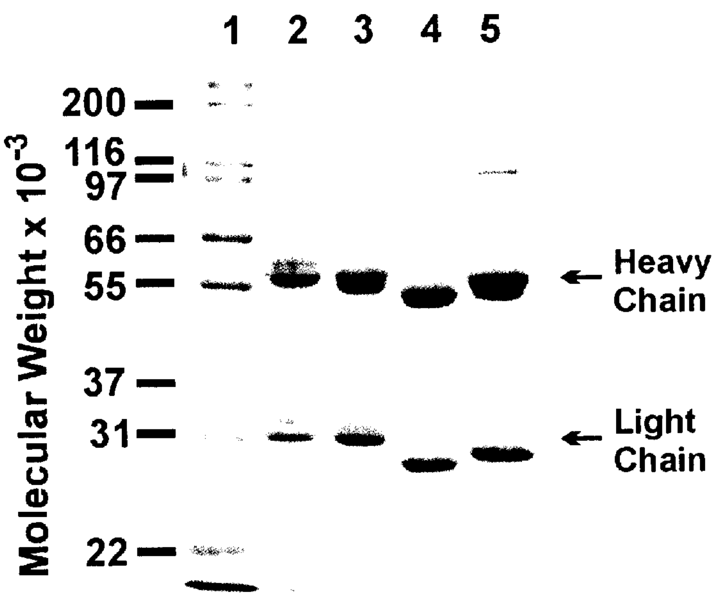
Lane 1 Molecular weight standards
Lane 2 Recombinant targeting antibody - Protein A purified
Lane 3 Recombinant targeting antibody - gel filtration purified
Lane 4 Mouse monoclonal antibody 44H104
Lane 5 Human $IgG_1$ FIG. 10A - Non-Reduced
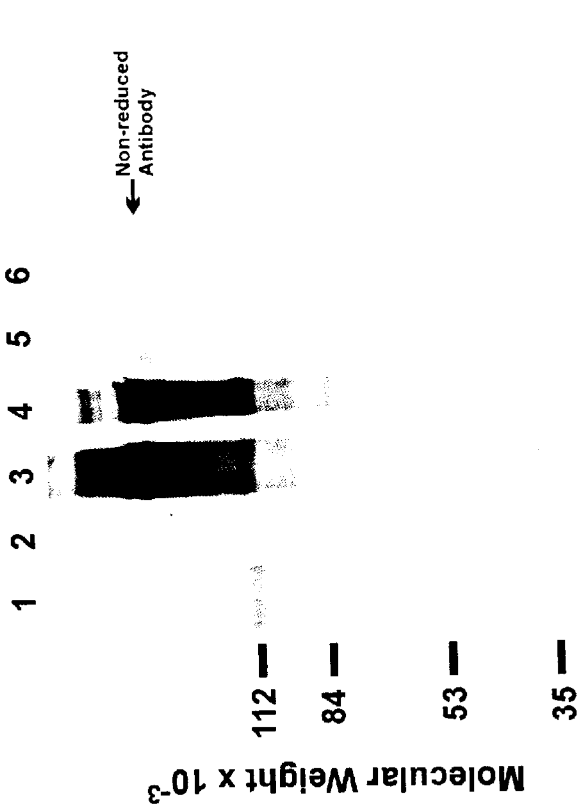
FIG. 10B - Reduced
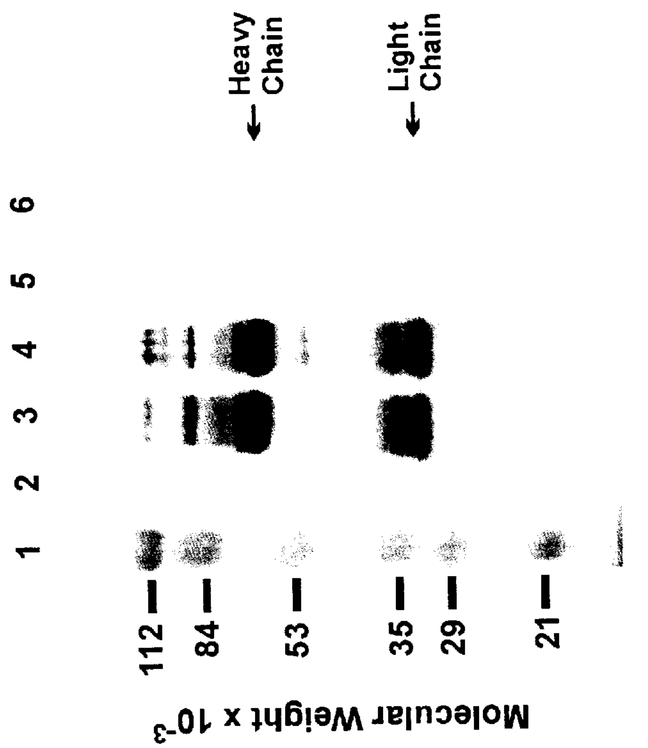
Lane 1 Molecular weight standards
Lane 2 Blank lane
Lane 3 Recombinant targeting antibody - Protein A purified
Lane 4 Recombinant targeting antibody - gel filtration purified
Lane 5 Mouse monoclonal antibody 44H104
Lane 6 Human $IgG_1$

SEQUENCE LISTING

```
(1) GENERAL INFORMATION:

   (iii) NUMBER OF SEQUENCES: 20


(2) INFORMATION FOR SEQ ID NO:1:

     (i) SEQUENCE CHARACTERISTICS:
          (A) LENGTH: 387 base pairs
          (B) TYPE: nucleic acid
          (C) STRANDEDNESS: single
          (D) TOPOLOGY: linear

    (xi) SEQUENCE DESCRIPTION: SEQ ID NO:1:

ATGGACATGA GGGTTCCTGC TCACGTTTTT GGCTTCTTGT TGCTCTGGTT TCCAGGTACC     60

AGATGTGACA TCCAGATGAC CCAGTCTCCA TCCTCCTTAT CTGCCTCTCT GGGACAAAGA    120

GTCAGTCTCA CTTGTCGGGC AAGTCAGGAA ATTAGTGGTT ACTTAACCTG GCTTCAGCAG    180

AAACCAGATG GAACTATTAA ACGCCTGGTC TACGCCGCGT CCACTTTAGA TTCTGGTGTC    240

CCAAAAAGGT TCAGTGGCAG TAGGTCTGGG TCAGATTATT CTCTCACCAT CAGCAGCCTT    300

GAGTCTGAAG ATTTTGCAGA CTATTACTGT CTACAATATA CTAATTATCC GCTCACGTTC    360

GGTGCTGGGA CCAAGCTGGA GCTGAAA                                        387


(2) INFORMATION FOR SEQ ID NO:2:

     (i) SEQUENCE CHARACTERISTICS:
          (A) LENGTH: 129 amino acids
          (B) TYPE: amino acid
          (C) STRANDEDNESS: single
          (D) TOPOLOGY: linear

    (xi) SEQUENCE DESCRIPTION: SEQ ID NO:2:

Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
            20                  25                  30

Leu Ser Ala Ser Leu Gly Gln Arg Val Ser Leu Thr Cys Arg Ala Ser
        35                  40                  45

Gln Glu Ile Ser Gly Tyr Leu Thr Trp Leu Gln Gln Lys Pro Asp Gly
    50                  55                  60

Thr Ile Lys Arg Leu Val Tyr Ala Ala Ser Thr Leu Asp Ser Gly Val
65                  70                  75                  80

Pro Lys Arg Phe Ser Gly Ser Arg Ser Gly Ser Asp Thr Ser Leu Thr
                85                  90                  95

Ile Ser Ser Leu Glu Ser Glu Asp Phe Ala Asp Tyr Tyr Cys Leu Gln
            100                 105                 110
```

-continued

```
Tyr Thr Asn Tyr Pro Leu Thr Phe Gly Ala Gly Thr Lys Leu Glu Leu
        115                 120                 125

Lys
```

(2) INFORMATION FOR SEQ ID NO:3:

(i) SEQUENCE CHARACTERISTICS:
(A) LENGTH: 420 base pairs
(B) TYPE: nucleic acid
(C) STRANDEDNESS: single
(D) TOPOLOGY: linear (xi) SEQUENCE DESCRIPTION: SEQ ID NO:3:

```
ATGGCTCTCC TGGTACTGTT CCTCTCCCTG GCTGCATTTC CAAGCTGTGG TGTCCTGTCC     60

CAGGTGCAGC TGAAGGAGTC AGGACCTGGC CTGGTGGCGC CCTCACAGAG CCTGTCCATC    120

ACTTGCACTG TCTCTGGGTT TTCATTAACC AGCTATGGTG TACACTGGGT TCGCCAGCCT    180

CCAGGAAAGG GTCTGGAGTG GCTGGGAGTA ATATGGGCTG GTGGAAGCAT AAATTATAAT    240

TCGGCTCTCA TGTCCAGACT GAGCATCAGC AAAGACAACT TCAAGAGCCA AGTTTTCTTA    300

AAAATGAGCA GTCTGCAAAC TGATGACACA GCCATGTACT ACTGTGCCAG AGCCTATGGT    360

GACTACGTCC ACTATGCTAT GGACTACTGG GGTCAAGGAA CCTCAGTCAC CGCCTCCTCA    420
```

(2) INFORMATION FOR SEQ ID NO:4:

(i) SEQUENCE CHARACTERISTICS:
(A) LENGTH: 140 amino acids
(B) TYPE: amino acid
(C) STRANDEDNESS: single
(D) TOPOLOGY: linear (xi) SEQUENCE DESCRIPTION: SEQ ID NO:4:

```
Met Ala Leu Leu Val Leu Phe Leu Ser Leu Ala Ala Phe Pro Ser Cys
1               5                   10                  15

Gly Val Leu Ser Gln Val Gln Leu Lys Glu Ser Gly Pro Gly Leu Val
            20                  25                  30

Ala Pro Ser Gln Ser Leu Ser Ile Thr Cys Thr Val Ser Gly Phe Ser
        35                  40                  45

Leu Thr Ser Tyr Gly Val His Trp Val Arg Gln Pro Pro Gly Lys Gly
    50                  55                  60

Leu Glu Trp Leu Gly Val Ile Trp Ala Gly Gly Ser Ile Asn Tyr Asn
65                  70                  75                  80

Ser Ala Leu Met Ser Arg Leu Ser Ile Ser Lys Asp Asn Phe Lys Ser
                85                  90                  95

Gln Val Phe Leu Lys Met Ser Ser Leu Gln Thr Asp Asp Thr Ala Met
            100                 105                 110

Tyr Tyr Cys Ala Arg Ala Tyr Gly Asp Tyr Val His Tyr Ala Met Asp
        115                 120                 125

Tyr Trp Gly Gln Gly Thr Ser Val Thr Ala Ser Ser
    130                 135                 140
```

(2) INFORMATION FOR SEQ ID NO:5:

(i) SEQUENCE CHARACTERISTICS:
(A) LENGTH: 34 amino acids
(B) TYPE: amino acid
(C) STRANDEDNESS: single
(D) TOPOLOGY: linear (xi) SEQUENCE DESCRIPTION: SEQ ID NO:5:

-continued

```
Gly Pro Lys Glu Pro Phe Arg Asp Tyr Val Asp Arg Phe Tyr Lys Asn
1               5                   10                  15

Lys Arg Lys Arg Ile His Ile Gly Pro Gly Arg Ala Phe Tyr Thr Thr
            20                  25                  30

Lys Asn


(2) INFORMATION FOR SEQ ID NO:6:

     (i) SEQUENCE CHARACTERISTICS:
          (A) LENGTH: 108 base pairs
          (B) TYPE: nucleic acid
          (C) STRANDEDNESS: single
          (D) TOPOLOGY: linear

    (xi) SEQUENCE DESCRIPTION: SEQ ID NO:6:

GGTCCTAAAG AACCTTTTAG AGACTATGTT GATAGGTTTT ATAAGAATAA GAGGAAGAGG     60

ATACATATAG GGCCTGGTAG GGCTTTTTAT ACTACTAAGA ATTAATAA                 108


(2) INFORMATION FOR SEQ ID NO:7:

     (i) SEQUENCE CHARACTERISTICS:
          (A) LENGTH: 60 base pairs
          (B) TYPE: nucleic acid
          (C) STRANDEDNESS: single
          (D) TOPOLOGY: linear

    (xi) SEQUENCE DESCRIPTION: SEQ ID NO:7:

CATTATGGAT CCGGTCCTAA AGAACCTTTT AGAGACTATG TTGATAGGTT TTATAAGAAT     60


(2) INFORMATION FOR SEQ ID NO:8:

     (i) SEQUENCE CHARACTERISTICS:
          (A) LENGTH: 51 base pairs
          (B) TYPE: nucleic acid
          (C) STRANDEDNESS: single
          (D) TOPOLOGY: linear

    (xi) SEQUENCE DESCRIPTION: SEQ ID NO:8:

GCCCTACCAG GCCCTATATG TATCCTCTTC CTCTTATTCT TATAAAACCT A              51


(2) INFORMATION FOR SEQ ID NO:9:

     (i) SEQUENCE CHARACTERISTICS:
          (A) LENGTH: 51 base pairs
          (B) TYPE: nucleic acid
          (C) STRANDEDNESS: single
          (D) TOPOLOGY: linear

    (xi) SEQUENCE DESCRIPTION: SEQ ID NO:9:

AGGGCCTGGT AGGGCTTTTT ATACTACTAA GAATTAATAA AAGCTTTAGC G              51


(2) INFORMATION FOR SEQ ID NO:10:

     (i) SEQUENCE CHARACTERISTICS:
          (A) LENGTH: 20 base pairs
          (B) TYPE: nucleic acid
          (C) STRANDEDNESS: single
          (D) TOPOLOGY: linear

    (xi) SEQUENCE DESCRIPTION: SEQ ID NO:10:

CATTATGGAT CCGGTCCTAA                                                 20


(2) INFORMATION FOR SEQ ID NO:11:

     (i) SEQUENCE CHARACTERISTICS:
```

-continued (A) LENGTH: 30 base pairs
(B) TYPE: nucleic acid
(C) STRANDEDNESS: single
(D) TOPOLOGY: linear (xi) SEQUENCE DESCRIPTION: SEQ ID NO:11:

GTCAGGTACC GGTCCTAAAG AACCTTTTAG 30

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:12:

GGCTAAAGCT TTTATTAATT C 21

(2) INFORMATION FOR SEQ ID NO:13:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:13:

AGCCTAAGCT TCCGCCATGG ACATGAGGGT TCCTGCTC 38

(2) INFORMATION FOR SEQ ID NO:14:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:14:

CCGTTTCAGC TCGAGCTTGG TCCCAGCACC GAA 33

(2) INFORMATION FOR SEQ ID NO:15:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:15:

CCTACTCGAG CTGAAACGGA CTGTGGCTGC ACCATCTGTC 40

(2) INFORMATION FOR SEQ ID NO:16:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:16:

ATTAAAGCTT TTACTAGGAT CCACACTCTC CCCTGTTGAA GCTC 44

(2) INFORMATION FOR SEQ ID NO:17:

(i) SEQUENCE CHARACTERISTICS:
(A) LENGTH: 36 base pairs

-continued

```
        (B) TYPE: nucleic acid
        (C) STRANDEDNESS: single
        (D) TOPOLOGY: linear

   (xi) SEQUENCE DESCRIPTION: SEQ ID NO:17:

AGCTAAGCTT CCGCCATGGC TCTCCTGGTA CTGTTC                          36


(2) INFORMATION FOR SEQ ID NO:18:

    (i) SEQUENCE CHARACTERISTICS:
        (A) LENGTH: 29 base pairs
        (B) TYPE: nucleic acid
        (C) STRANDEDNESS: single
        (D) TOPOLOGY: linear

   (xi) SEQUENCE DESCRIPTION: SEQ ID NO:18:

GCGCACTAGT TCCTTGACCC CAGTAGTCC                                  29


(2) INFORMATION FOR SEQ ID NO:19:

    (i) SEQUENCE CHARACTERISTICS:
        (A) LENGTH: 52 base pairs
        (B) TYPE: nucleic acid
        (C) STRANDEDNESS: single
        (D) TOPOLOGY: linear

   (xi) SEQUENCE DESCRIPTION: SEQ ID NO:19:

GCGCACTAGT GTCACCGCCT CCTCAGCCTC CACCAAGGGC CCATCGGTCT TC        52


(2) INFORMATION FOR SEQ ID NO:20:

    (i) SEQUENCE CHARACTERISTICS:
        (A) LENGTH: 43 base pairs
        (B) TYPE: nucleic acid
        (C) STRANDEDNESS: single
        (D) TOPOLOGY: linear

   (xi) SEQUENCE DESCRIPTION: SEQ ID NO:20:

ACGCAAGCTT TTACTAGGTA CCTTTACCCG GAGACAGGGA GAG                  43
```

METHOD FOR DELIVERY OF ANTIGENS TO SELECTED CELLS OF THE IMMUNE SYSTEM USING CHIMERIC ANTIBODIES

REFERENCE TO RELATED APPLICATION

The present application is a continuation of Application Ser. No. 08/483,576 filed Jun. 7, 1995 (now abandoned).

FIELD OF INVENTION

The present invention is concerned with novel recombinant antibody molecules genetically modified to contain an antigen moiety for the purpose of delivery of the antigen moiety to antigen-presenting cells of the immune system.

BACKGROUND OF INVENTION

Current theories of immunology suggest that, in order to provide a potent antibody response, an antigen must be seen by both B cells, which subsequently develop into the antibody producing cells, and also by helper T-cells, which provide growth and differentiation signals to the antigen specific B-cells. Helper T-cells recognize the antigen on the surface of antigen-presenting cells (APC) in association with Class II major histocompatibility complex (MHC) gene products.

There are significant advantages in using proteins and peptides derived from proteins of infectious organisms as part of subunit vaccines. The search for such suitable subunits constitutes a very active area of both present and past research. Advances in techniques of recombinant DNA manipulations, protein purification, peptide synthesis and cellular immunology have greatly assisted in this endeavour. However, a major stumbling block to the use of such materials as vaccines has been the relatively poor in-vivo immunogenicity of most protein subunits and peptides. Generally, the immune response to vaccine preparations is enhanced by the use of adjuvants. However, the only currently licensed adjuvants for use in humans are aluminum hydroxide and aluminum phosphate, collectively termed alum, which is limited in its effectiveness as a potent adjuvant. There is thus a need for new adjuvants with the desired efficacy and safety profiles.

Several adjuvants, such as Freund's Complete Adjuvant (FCA), syntex and QS21, have been used widely in animals (ref 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). In animals, administration of peptides and protein antigens with these adjuvants, has been shown to result in neutralizing antibodies against a variety of infectious organisms (refs. 3 to 8). A novel way of engaging both the B and T cell components of an immune response has been described, which uses anti-class II monoclonal antibodies (mabs) coupled to antigens to target class II bearing antigen presenting cells (APC's) (refs 9 to 11, also U.S. Pat. Nos. 5,194,254 and 4,950,480, assigned to the assignee hereof). Experiments carried out in-vivo in rodents and rabbits using this technology, (refs. 9 to 12), have demonstrated convincing proof of enhancement in immunogenicity of antigens, in the absence of conventional adjuvants. Several research groups have used other cell surface markers such as Surface Immunoglobulin (sIg) (ref. 13), Fc γ receptors, CD45 and MHC class I (refs. 14 to 17), to achieve targeting to APC's; however, most of these latter studies involve in-vitro experiments and lack animal data. Another group of studies reports the use of antibodies of irrelevant specificity to carry antigen epitopes (refs. 18 to 24). The in-vivo studies utilizing such "antigenized antibodies", however, involves the use of conventional adjuvants and some of them require multiple injections for the desired effect (ref. 24).

In previous studies using anti-class II mab as a targeting molecule (refs. 9 to 11), biotin-streptavidin based interaction was used to link the antibody and antigen. There are some inherent disadvantages with such chemical coupling techniques, such as yields (about 20%) and also the variability factor between different preparations. There is also no adequate control on the amounts of coupled peptide as well as the exact location of the reaction. Additionally, further purification is usually required and, therefore, losses in material can be significant.

Recently a study reporting in-vitro data using antihuman class II Fab-peptide fusions generated by recombinant DNA methodology, has been published (ref. 27). There are several differences between these fusions and the present invention in that the former is an *E. coli* expressed monovalent protein fragment of a divalent whole immunoglobulin molecule and also is an in-vitro study. The common problems encountered in bacterial expression systems include expression as inclusion bodies which require solubilization and refolding with extensive product losses. The expression of whole antibody is presently not possible in *E. coli* and, therefore, the monovalent Fab may not have the requisite affinity for in-vivo targeting. There are, thus, several advantages in using a whole IgG recombinant system as described herein.

There remains a need, therefore, to produce conjugates of targeting antibodies and antigens of specific reproducible structure in high yields. Such conjugate antibody molecules and nucleic acid molecules encoding the same are useful in immunogenic preparations including vaccines, for protection against disease caused by a selected pathogen and for use as and for the generation of diagnostic reagents and kits.

SUMMARY OF INVENTION

The present invention includes novel recombinant conjugate antibody molecules which have been genetically modified to contain an antigen moiety for delivery of the antigen moiety to antigen-presenting cells of the immune systems.

Accordingly, in one aspect of the present invention, there is provided a conjugate antibody molecule, comprising a monoclonal antibody moiety specific for a surface structure of antigen-presenting cells genetically modified to contain at least one antigen moiety exclusively at at least one preselected site in the monoclonal antibody. The conjugate antibody molecule is capable of delivering the antigen moiety to the antigen presenting cells of a host and capable of eliciting an immune response to the antigen moiety in the host.

Genetically modifying the antibody moiety to contain the antigen moiety only at preselected sites ensures that a product with consistent composition and structure is obtained.

The antigen presenting cells may be any convenient antigen-presenting cells of the immune system, including class I or class II major histocompatibility expressing cells (MHC), B-cells, T-cells or professional antigen-presenting cells including dendritic cells, and $CD4^+$ cells.

The at least one antigen moiety preferably is located at at least one end of at least one of the heavy and light chain of the monoclonal antibody moiety, particularly the C-terminal end of both the heavy and light chains. The at least one antigen moiety is preferably directly linked with the C-terminal end of both the heavy and light chains of the monoclonal antibody moiety.

One feature of the present invention is the ability to obtain an enhanced immune response to an antigen without the use of an adjuvant. Accordingly, in one embodiment of the invention, the at least one antigenic moiety may comprise an inherently weakly-immunogenic antigen moiety. The at least one antigen moiety may comprise a plurality of antigen moieties, which may be the same or different. In addition, the at least one antigen moiety may be a peptide having 6 to 100 amino acids and containing at least one epitope.

The novel conjugate antibody molecules provided herein are produced by recombinant procedures which include the provision of novel nucleic acid molecules and vectors containing the same.

In accordance with another aspect of the present invention, there is provided a nucleic acid molecule comprising a first nucleotide sequence encoding a chain of a monoclonal antibody specific for a surface structure of antigen-presenting cells selected from the group consisting of the heavy chain and the light chain of the monoclonal antibody, a second nucleotide sequence encoding at least one antigen and a third nucleotide sequence comprising a promoter for eukaryotic cell expression of a fusion protein comprising said monoclonal antibody chain and said at least one antigen. The antigen presenting cells may be any of those described above.

The first nucleotide sequence and the second nucleotide sequence are preferably directly linked in a single transcriptional unit under control of the promoter. The third nucleotide sequence preferably is disposed at the 5'-end of the first nucleotide sequence.

The present invention further includes vectors comprising the nucleic acid molecules provided herein. In one specific embodiment of this aspect of the invention, this vector may contain a first nucleic acid molecule comprising a first nucleotide sequence encoding the heavy chain of a monoclonal antibody specific for a surface structure of antigen-presenting cells, a second nucleotide sequence encoding at least one antigen and a third nucleotide sequence comprising a promoter for eukaryotic cell expression of a fusion protein comprising said monoclonal antibody heavy chain and said at least one antigen as a first transcriptional unit, and a second nucleic acid molecule comprising a first nucleotide sequence encoding the light chain of a monoclonal antibody specific for a surface structure of antigen-presenting cells, a second nucleotide sequence encoding at least one antigen and a third nucleotide sequence comprising a promoter for eukaryotic cell expression of a fusion protein comprising said monoclonal antibody light chain and said at least one antigen as a second transcriptional unit.

One particular vector has the characteristics of plasmid pCMVdhfr.chLCHC (ATCC Accession No. 97,202).

The production of the conjugate antibody molecule comprising a monoclonal antibody moiety specific for a surface structure of antigen-presenting cells and at least one antigen moiety in mammalian cells constitutes a further aspect of the invention. Such procedure comprises:

constructing a first nucleic acid molecule containing a first nucleotide sequence encoding a heavy chain of said monoclonal antibody and a second nucleotide sequence encoding at least one antigen, constructing a second nucleotide acid molecule containing a first nucleotide sequence encoding a light chain of said monoclonal antibody and a second nucleotide sequence encoding said at least one antigen, and coexpressing said first and second nucleic acid molecules in mammalian cells to form said conjugate antibody molecule.

The coexpression of the first and second nucleic acid molecules includes constructing an expression vector containing the first and second nucleic acid molecules as independent transcriptional units, which preferably also contain a promoter operable in mammalian cells to direct the coexpression. The coexpression includes secretion of the conjugate molecule and the conjugate molecules may be separated from the culture medium and purified, preferably by binding to protein A and selectively eluting the conjugate molecules.

A further aspect of the invention provides an immunogenic composition comprising a conjugate antibody molecule as provided herein or a nucleic acid molecule as provided herein. The immunogenic composition preferably is formulated as a vaccine for in vivo administration to a host to elicit an immune response against disease(s) caused by a pathogen producing the at least one antigen.

According to an additional aspect of the invention, there is provided a method of generating an immune response in a host, comprising administering thereto an immunoeffective amount of a immunogenic composition as provided herein.

The novel conjugate antibody molecules provided herein also are useful in diagnostic applications. Accordingly, in yet a further aspect of the invention, there is provided a method of determining the presence of a selected antigen in a sample, which comprises:

(a) immunizing a host with a conjugate antibody molecule as provided herein, wherein the at least one antigen moiety is said selected antigen to produce antibodies specific to the selected antigen;

(b) isolating the antibodies;

(c) contacting the sample with the isolated antibodies to produce complexes comprising any selected antigen in the sample and the selected antigen-specific antibodies; and (d) determining production of the complexes.

The invention further comprises a diagnostic kit for determining the presence of a selected antigen in a sample, comprising:

(a) a conjugate antibody molecule as provided herein, wherein the at least one antigen moiety is the selected antigen;

(b) means for detecting the production of complexes comprising any selected antigen in the sample and selected antigen-specific antibodies to said selected antigen; and (c) means for determining production of the complexes.

The invention further includes methods for producing antibodies specific for a selected antigen. One such procedure comprises:

(a) immunizing a host with an effective amount of an immunogenic composition as provided herein, wherein the at least one antigen is a selected antigen to produce antibodies specific for the selected antigen; and (b) isolating the antibodies from the host. Another such procedure comprises:

(a) administering an immunogenic composition as provided herein, wherein said at least one antigen is a selected antigen, to at least one mouse to produce at least one immunized mouse;

(b) removing B-lymphocytes from the at least one immunized mouse;
(c) fusing the B-lymphocytes from the at least one immunized mouse with myeloma cells, thereby producing hybridomas;
(d) cloning the hybridomas;
(e) selecting clones which produce anti-selected antigen antibody;
(f) culturing the anti-selected antigen antibody-producing clones; and then
(g) isolating anti-selected antigen antibodies from the cultures.

BRIEF DESCRIPTION OF DRAWINGS

The invention is described in more detail herein with reference to the accompanying drawings, in which:

FIG. 1A shows the DNA sequence (SEQ ID No: 1) and derived amino acid sequence (SEQ ID No: 2) of the variable region of murine 44H104 mab light chain. The sequence of the peptide mediating secretion is shown in italicized script.

FIG. 1B shows the DNA sequence (SEQ ID No: 3) and derived amino acid sequence (SEQ ID No: 4) of the variable region of murine 44H104 mab heavy chain. The sequence of the secretory peptide mediating secretion is shown in italicized script.

FIG. 2C shows synthetic polynucleotides CTLB 36.1, CTLB 36.2 and CTLB 36.3 and their sequences (SEQ ID Nos: 7, 8 and 9) used in the scheme of FIG. 2B and primers LC.F, HC.F and R and their sequences (SEQ ID Nos: 10, 11 and 12) used in the PCR reaction.

FIG. 3B shows the oligonucleotide primers Pr. 1, Pr. 2, Pr. 3 and Pr. 4 (SEQ ID Nos: 13, 14, 15 and 16) synthesized for PCR reactions to obtain $V_L$ and $C_L$ gene cassettes.

FIG. 4B shows the oligonucleotide primers Pr. 5, Pr. 6, Pr. 7 and Pr. 8 (SEQ ID Nos: 17, 18, 19 and 20) synthesized for PCR reactions to obtain $V_H$ and $C_H$ gene cassettes.

FIGS. 9A and 9B depict Coomassie blue stained SDS/PAGE gels 7.5% (FIG. 9A) and 10% (FIG. 9B). Gel A was run with samples in non-reducing buffer and gel B in reducing buffer. The bands corresponding to the intact antibody (FIG. 9A) and light and heavy chains (FIG. 9B) are labelled with arrows.

FIGS. 10A and 10B depict Western blots corresponding to the Coomassie blue stained gels of FIG. 9. The bands corresponding to intact antibody conjugate (FIG. 10A) and light and heavy chain conjugates (FIG. 10B) are indicated with arrows. The primary antibody reagent used was anti-CLTB36 guinea pig anti-sera.

GENERAL DESCRIPTION OF INVENTION

Figures 2A, 2B:
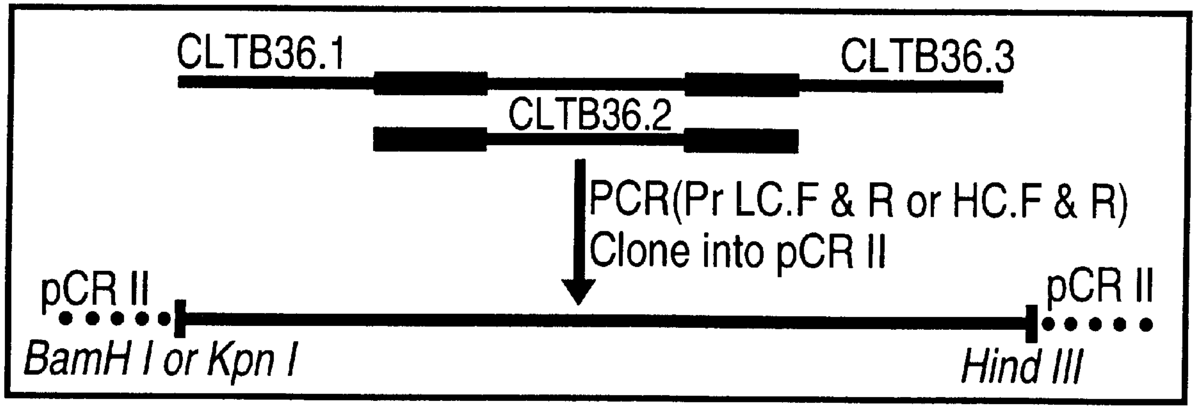
FIG. 2A shows the amino acid sequence (SEQ ID No: 5), in single letter code of peptide CTLB36, and nucleotide sequence encoding the same (SEQ ID No: 6), including two termination codons.
FIG. 2B shows a scheme for construction and assembly of a gene coding for CTLB36 using overlap extension PCR.

In the present invention, an antigen, against which it is desired to raise antibodies in a host, generally is conjugated to the C-terminus of both the light and heavy chains of a monoclonal antibody, which is specific for a particular surface structure of antigen-presenting cells. This arrangement allows for delivery of the antigen to the relevant cells in the immune system upon injection of the conjugate to a host. The monoclonal antibody, therefore, acts as a "vector" or "delivery vehicle" for targeting antigenic determinants to antigen presenting cells, thereby facilitating their recognition by T-helper cells. The antigen presenting cells possess a variety of specific cell surface structures or markers which are targeted by any particular monoclonal antibody. Thus, antigens may be conjugated to a monoclonal antibody specific for any of the surface structures on the antigen presenting cells, including class I and class II major histocompatibility complex (MHC) gene products.

The surface structures on the antigen presenting cells of the immune system which can be recognized and targeted by the monoclonal antibody portion of the immunoconjugates are numerous and the specific surface antigen structure targeted by the monoclonal antibody depends on the specific monoclonal antibody.

The monoclonal antibody may be specific for a gene product of the MHC, and, in particular, may be specific for class I molecules of MHC or for class II molecules of MHC. However, the invention is not limited to such specific surface structures and the conjugates containing the corresponding monoclonal antibodies, but rather, as will be apparent to those skilled in the art, the invention is applicable to any other convenient surface structure of antigen presenting cells which can be recognized and targeted by a specific monoclonal antibody to which an immunogenic molecule is conjugated.

For example, strong adjuvant-independent serological responses to a delivered antigen can be obtained with conjugates formed with dendritic cell-specific monoclonal antibody and $CD4^+$ cell-specific monoclonal antibody.

In the present invention, the monoclonal antibody specific for the target structure is provided in the form of a conjugate with an antigen against which it is desired to elicit an immune response conveniently joined to the C-terminal of the heavy and/or light chains of the monoclonal antibody. While the conjugate antibody molecules are illustrated by such C-terminal connection, the antigen moiety alternatively may be inserted within the light and heavy chains of the antibody and such insertions may establish a particular constrained conformation of the antigen and, in particular, epitopes, within the known structural framework of an antibody molecule. Such conjugate antibody molecules may be conveniently produced by genetic modification of a gene encoding the heavy and light chains of the antibody to contain a gene encoding one or more antigen (s) and coexpressing the resulting nucleic acid molecules.

The invention is particularly useful for antigen molecules which normally possess a weakly-immunogenic response, since that the response is potentiated by the present invention. The antigen molecule may be in the form of a peptide or protein, as discussed above, but is not limited to such materials.

The present invention is applicable to any antigen which it is desired to target to antigen presenting cells using the monoclonal antibody. The antigen may be a protein or a peptideof 6 to 100 amino acids comprising an amino acid sequence of an epitope. Representative organisms from which the antigen may be derived include influenza viruses, parainfluenza viruses, respiratory viruses, measles viruses, mumps viruses, human immunodeficiency viruses, polio viruses, rubella viruses, herpex simplex viruses type 1 and 2, hepatitis viruses types A, B and C, yellow fever viruses, smallpox viruses, rabies viruses, vaccinia viruses, reo viruses, rhinoviruses, Coxsackie viruses, Echoviruses, rotaviruses, papilloma viruses, paravoviruses and adenoviruses, *E. coli, V. cholera*, BCG, *M. tuberculosis, C. diphtheria, Y. pestis, S. typhi, B. pertussis, S. aureus, S. pneumoniae, S. pyogenes, S. mutans*, Myocoplasmas, Yeasts, *C. tetani*, meningococci (e.g., *N. meningitidis*), Plasmodium spp, Mycobacteria spp, Shigella spp, Campylobacter spp, Proteus spp, *Neisseria gonorrhoea*, and *Haemophilus influenzae*. The antigen moiety may also be derived from hormones, such as human HCG hormone, and tumor-associated antigens.

The present invention attempts to address some of the problems of the prior art, referred to above, by incorporating a peptide antigen, at the C-terminus of light and heavy chains of the targeting antibody by recombinant DNA means. The model peptide used herein is CLTB36, which is a tandem T-B HIV peptide found to elicit neutralizing responses in several animals (as described in copending U.S. Ser. No. 08/257,528 filed Jun. 9, 1994, assigned to the assignee hereof and the disclosure of which is incorporated herein by reference and corresponding International Publication No. WO 94/29339), although the principles of the invention are applicable to any antigen. The DNA sequence encoding this peptide is incorporated at the 3' ends of the genes encoding a mouse/human chimeric anti-human class II mab (44H104), When these genes are included in a suitable expression vector and expressed, a recombinant chimeric anti-human class II/antigen fusion is obtained. This may be purified easily in a single step by Protein A affinity purification or other suitable procedure.

The present disclosure reports the in-vivo responses of macaques to a priming and boosting dose of anti-class II chimeric antibody/CLTB36 fusion generated by recombinant means. The genes for the fusion protein were generated by polymerase chain reaction (PCR) using cloned cDNA and synthetic oligonucleotides. The antigen (CLTB36) gene was constructed using overlap extension PCR. The genes were cloned into an expression vector, transfected into YB2/0 cells and gene amplification carried out using a murine dhfr cassette cloned into the same expression plasmid. Several clones secreting adequate levels of the properly folded and assembled product were identified. The antigen fusions at the C-terminus of the light and heavy chain do not affect the proper assembly of the antibody (see FIG. 9) which also maintains its binding specificity (see FIG. 6).

As described in U.S. Pat. Nos. 4,950,480 and 5,194,254, coupling a weak antigen to the specific monoclonal antibody results in an enhancement of the immunogenicity of such antigen, while avoiding the use of adjuvants and hence represents a much safer immunization procedure which can utilize materials from which only a weak immune response is achieved. Examples of such materials are small peptides which are epitopes of larger proteins or are protein subunits of a pathogen.

For human use, it is desirable that the antibody be modified to produce a mouse/human chimeric antibody, since extensive anti-murine monoclonal antibody responses would be generated by administration of a murine antibody to humans. Since the invention is broadly applicable to any species, it is desirable that, when a conjugate antibody molecule is administered to a specific species, the murine antibody sequences be replaced by corresponding sequences from the specific species in an analogous manner to that described herein for the mouse/human chimeric antibodies.

The experimental data presented herein and detailed in the Examples below demonstrate the ability of a mouse/human chimeric antibody, which targets antigen presenting cells (APC's) of the immune system via their surf ace MHC class II receptors, to enhance the immune response to a peptide antigen conjugated to the C terminus of both the light and heavy chains. Such a conjugate can be produced conveniently, as detailed in the Examples, using recombinant DNA methodology, namely by assembling the genes encoding both the light and heavy chains with CLTB36 or other antigen of interest in a suitable expression vector. The vector pRC/CMV was selected as the basic expression plasmid in the experimental work performed herein, since it uses the powerful and broad host range immediate early CMV promoter to drive transcription. The final construct was designed to contain both light and heavy chain genes on the same vector as independent transcriptional units. The murine dhfr gene encoding cassette was also incorporated in this specific vector to provide a suitable means of gene amplification. This expression vector was electroporated into rat myeloma YB2/0 cells. Cell lines expressing recombinant antibody were established. Using the amplification procedure outlined in the Examples below and reported in the literature (ref. 32) stable cell lines secreting viable amounts of recombinant antibody conjugate (approximately 30 $\mu$g/ml) established relatively quickly (in about 4 months). The recombinant chimeric conjugate is assembled correctly and has the same specificity as the parent mab 44H104.

The recombinant conjugate, when administered to macaques without an extrinsic adjuvant (e.g. alum or syntex), elicits good priming immune response, as measured by IgG titres to the peptide antigen on the conjugate. This response is also directed towards the native antigen as measured by recombinant P24 reactivity. The priming response fades after a while but was boosted in two out of three animals by another dose of the chimeric mab conjugate in PBS.

The experimental data presented herein and detailed below, demonstrates the enhancement of immune response to a peptide antigen in the absence of conventional adjuvants, by coupling to an anti-class II chimeric antibody, the conjugate being generated by recombinant means. The conjugate can be obtained in large amounts by expression in cells, such as YB2/O cells.

It is clearly apparent to one skilled in the art, that the various embodiments of the present invention have many applications in the fields of vaccination, diagnosis and treatment of diseases produced by selected pathogens. A further non-limiting discussion of such uses is further presented below.

1. Vaccine Preparation and Use

Immunogenic compositions, suitable to be used as vaccines, may be prepared from the conjugate antibody molecules as disclosed herein. The vaccine elicits an immune response in a subject which produces antibodies including anti-antigen moiety antibodies. Should the vaccinated subject be challenged by a pathogen that produces the antigen moiety, the antibodies bind to and inactivate the pathogen.

Immunogenic compositions including vaccines may be prepared as injectables, as liquid solutions or emulsions. The conjugate antibody molecules may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, or pH buffering agents. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the conjugate antibody molecules. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune-system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms or milligrams of the conjugate antibody molecules. Suitable regimes for initial administration and booster doses are also variable, but may include an initial administration followed by subsequent administrations. The dosage may also depend on the route of administration and will vary according to the size of the host.

The concentration of antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

The nucleic acid molecules encoding the conjugate antibody molecules of the present invention may also be used directly for immunization by administration of the DNA directly, for example, by injection for genetic immunization. Processes for the direct injection of DNA into test subjects for genetic immunization are described in, for example, Ulmer et al, 1993 (ref. 33).

2. Immunoassays

The conjugate antibody molecules of the present invention are useful as immunogens for the generation of anti-antigen moiety antibodies (including monoclonal antibodies for use in immunoassays including enzyme—linked immunosorbent assays (ELISA), RIAs and other non-enzyme linked antibody binding assays or procedures known in the art. In ELISA assays, the anti-antigen moiety antibodies are immobilized onto a selected surface, for example, a surface capable of binding proteins such as the wells of a polystyrene microtiter plate. After washing to remove incompletely adsorbed antibodies, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of test sample onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound anti-antigenic moiety antibodies, and subsequent washing, the occurrence, and even amount, of immunocomplex formation may be determined.

BIOLOGICAL DEPOSITS

Plasmid pCMVdhfr.chLCHC that contains portions coding for conjugate antibody molecules that is described and referred to herein has been deposited with the American Type Culture Collection (ATCC) located at 10801 University Blvd., Manassas, Va. 20110-2209, U.S.A. pursuant to the Budapest Treaty and prior to the filing of this application, under Accession No. 97,202 on Jun. 23, 1995. Samples of the deposited plasmid will become available to the public upon grant of a patent based upon this United States patent application and all restrictions upon the availability of the deposit will be removed at that time. The invention described and claimed herein is not to be limited in scope by the plasmid deposited, since the deposited embodiment is intended only as an illustration of the invention. Any equivalent or similar plasmids that encode similar or equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Enzymes and reagents commonly used in standard recombinant DNA technology manipulations were purchased from Boehringer Mannheim, New England Biolabs, Gibco/BRL and Pharmacia. Many specific reactions were performed using Reagent Kits which were purchased from several sources indicated in the specific Examples below. Antibody reagents for ELISAs were purchased from Caltag unless otherwise indicated. Plasmid vectors were purchased from Gibco/BRL or Invitrogen. Polymerase Chain Reaction (PCR) was performed using protocols and kits GENE AMP PCR SYSTEM (trademark) supplied by Perkin Elmer Cetus. The Thermal cycler used in PCR reactions was purchased from Perkin Elmer Cetus.

The synthesis of oligonucleotides was carried out using an Applied Biosystems 380B DNA synthesizer. The synthesized oligonucleotides were purified on OPC cartridges supplied by Applied Biosystems following the manufacturers protocols. DNA sequencing was performed on an automated DNA sequencer (370A; Applied Biosystems), using the dideoxy terminator chemistry and reagents supplied by the manufacturer.

Example 1

This Example illustrates cDNA synthesis and sequence determination.

The hybridoma cell line 44H104 secreting murine anti-human class II mab (IgG2aK) was grown in RPMI medium, (Gibco-BRL) supplemented with glutamine (2 mM), penicillin (50 ug/ml) and streptomycin (50 U/ml) and containing 10% FBS. Cells ($10^6$) were harvested and mRNA isolated using a 'FAST TRACK (trademark) mRNA Isolation', kit (Invitrogen). First and second-strand cDNA was prepared using the 'cDNA SYNTHESIS PLUS (trademark)' kit (Amersham) and protocols supplied by the manufacturer. The cDNA generated in this step was cloned into λgt10 using the 'cDMA CLONING SYSTEM-λgt10 (trademark)' kit (Amersham) to generate a lamda phage cDNA library. A cDNA library from the mRNA of mab 44H104 secreting cell line was made in lambda phage. Phage clones containing genes encoding the light and heavy chains were identified. PCR reactions were also performed on the cDNA (50 ng) using primers and conditions used by Winter and colleagues (Ref 28). The amplified products corresponding to $V_L$ and $V_H$ of 44H104 were labelled with $P^{32}$ using the 'RANDOM PRIMING SYSTEM 1 (trademark)' kit (New England Biolabs) and used as probes to isolate phage clones containing inserts encoding the light and heavy chain genes.

The inserts were excised and cloned into the multilinker region of pUC18. These were sequenced and the nucleotide sequence of both $V_L$ and $V_H$ are displayed in FIGS. 1 and 1B respectively (SEQ ID Nos: 1 and 2). The italicised sequences in this figure are the sequences of the signal peptide which precede the mature sequences of the light and heavy chains. Most standard manipulations were performed using well described protocols (ref. 29).

Example 2

This Example illustrates construction of a gene encoding peptide antigen CTLB36.

Antigen peptide CLTE36 (FIG. 2A, SEQ ID No: 5), which consists of a tandemly linked T and B cell epitope, derived from the sequence of MN strain of HIV, was constructed by PCR using the overlap extension method (illustrated in FIG. 2B). The nucleic acid sequence encoding CLTB36 was deduced from the amino acid sequence of the peptide antigen (FIG. 2A, SEQ ID No: 6). The procedure consists of synthesizing three oligonucleotides (CLTB36.1, CLTB36.2 and CLTB36.3; FIG. 2C, SEQ ID Nos: 7, 8 and 9) which span the entire gene. The oligonucleotide CLTB36.1 was designed to have 16 bases at the 3' end, complementary (overlap) to the 5' end of CLTB36.2, which in turn has a 16 base overlap at its 3' end with corresponding 5' nucleotides of oligonucleotide CLTB36.3. Polynucleotide primers designated as PrLC.F and PrHC.F were also synthesized; these were designed to overlap with the 5' of the gene coding for CLTB36 and provide a BamHI site for incorporation into the light chain gene or a Kpn I site for fusion with the heavy chain gene (FIG. 2C, SEQ ID Nos: 10 and 11). The last primer(Pr.R) is the 'back' primer and has homology to the 3' end of the CLTB36 gene and was designed to provide a Hind III site for cloning into the expression plasmid (FIG. 2C, SEQ ID No: 12).

The oligonucleotides CLTB36.1, CLTB36.2, and CLTB36.3 were mixed together (30 pm each) in PCR reaction buffer heated up to 90° C. and slowly annealed at about 45° C. Subsequently the volume was made up to 100 μl by adequate additions of buffer, dNTP's primers (PrLC.F and PrR for light chain antigen; PrHC.F and Pr.R for heavy chain antigen; 100 pmol each) using material and protocols from a Gene Amp PCR kit and a PCR reaction was performed. The aqueous phase of the reaction mixture was removed to another tube and an aliquot (5 μl) was ligated into pCRII vector and cloned using a 'TA cloning kit' (Invitrogen). The insert was sequenced and clones containing the correct sequence excisable by the correct combination of restriction sites were established.

Example 3

This Example illustrates assembly of the gene encoding the chimeric light chain of 44H104 conjugated to mab CTLB36.

Figure 3A:
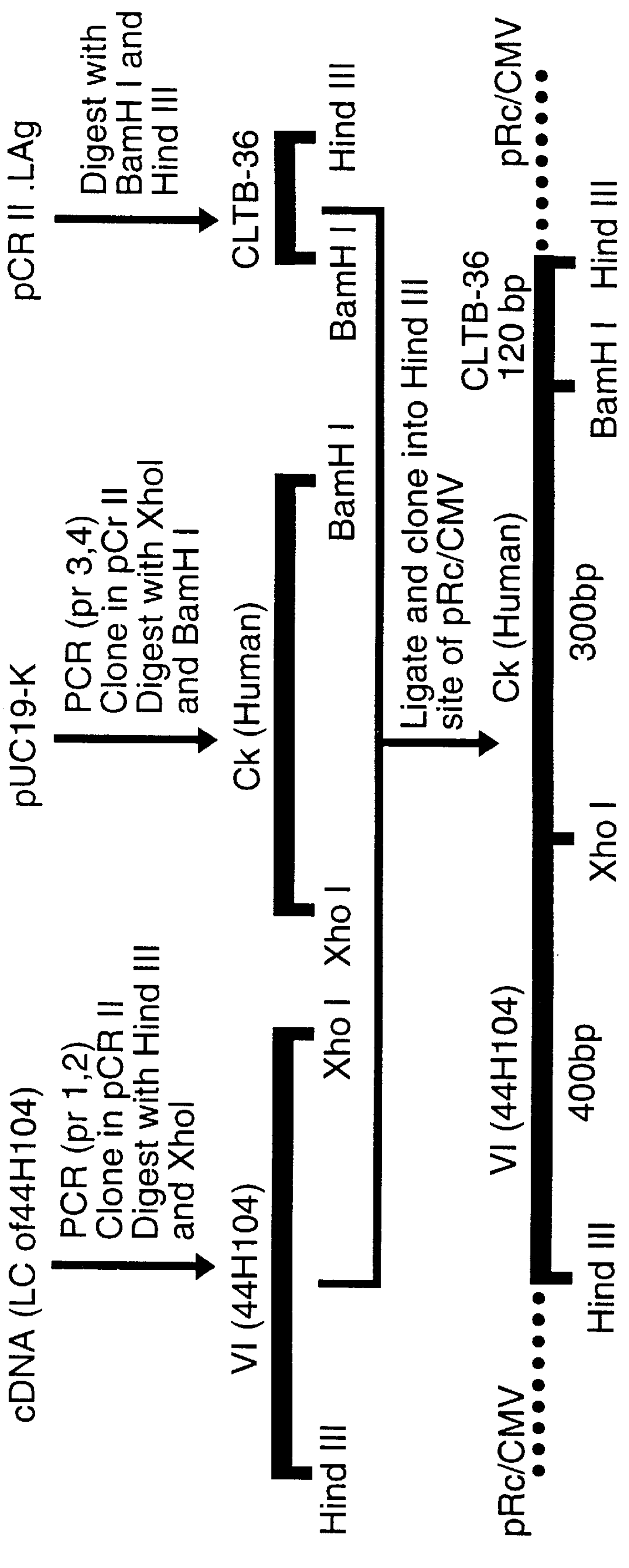
FIG. 3A shows a scheme for construction of 44H104 light chain gene using PCR-generated DNA cassettes $V_L$ and $C_L$.

The $V_L$ of 44H104 and its natural signal sequence was obtained by PCR amplification using pUC18·LC (pUC18 vector containing a light chain encoding cDNA insert) as a template. The two primers used in the reaction (Pr 1 and 2; FIG. 3B, SEQ ID Nos: 13, 14) were designed to (a) incorporate a Hind III restriction site followed by a Kozak consensus sequence (CCGCC; ref. 3) at the 5' of the amplified product and (b) incorporate an xho I restriction site at the junction of $V_L$ and $C_L$ by creating a silent mutation. The PCR reactions were carried out using 50 ng of template, 100 pmol each of the primers in a 100 μl volume using buffers, dNTP's and enzyme supplied in the GeneAmp kit. The cycling parameters were: 95° C. for 1 min., 55° C. for 1 min. followed by 72° C. for 2 min., for a total of 25 cycles. An aqueous aliquot of the final reaction mixture was analyzed on a 10% agarose gel and another aliquot (5 μl) was ligated into pCRII vector supplied in the 'TA Cloning' kit (Invitrogen). The ligation reaction was used to transform competent *E. coli* cells plated out on X-Gal agar plates containing ampicillin. Plasmid was isolated from several colonies bearing a white phenotype and sequenced. Approximately one in three clones were found to have the correct sequence.

The human light chain constant (Kappa) gene required for the construct encoding chimeric 44H104 light chain was also obtained by PCR amplification. The template was a plasmid pUC19-k containing an insert coding for the human kappa gene. The primers used in the PCR reaction (pr. 3 and 4; FIG. 3B, SEQ ID Nos: 15 and 16) were designed to incorporate an Xho I restriction site at the 5' end of the cassette suitable for ligation with the VL gene obtained above. These primers also incorporate a BamHI site at the 3' end to enable ligation to the antigen-CLTB36 gene. The PCR reaction was carried out in the same way as described above for $V_L$ gene of 44H104, cloned into pCRII vector and clones carrying inserts identified and sequenced. Two clones having the correct sequence were set aside for further work.

Figure 5A:
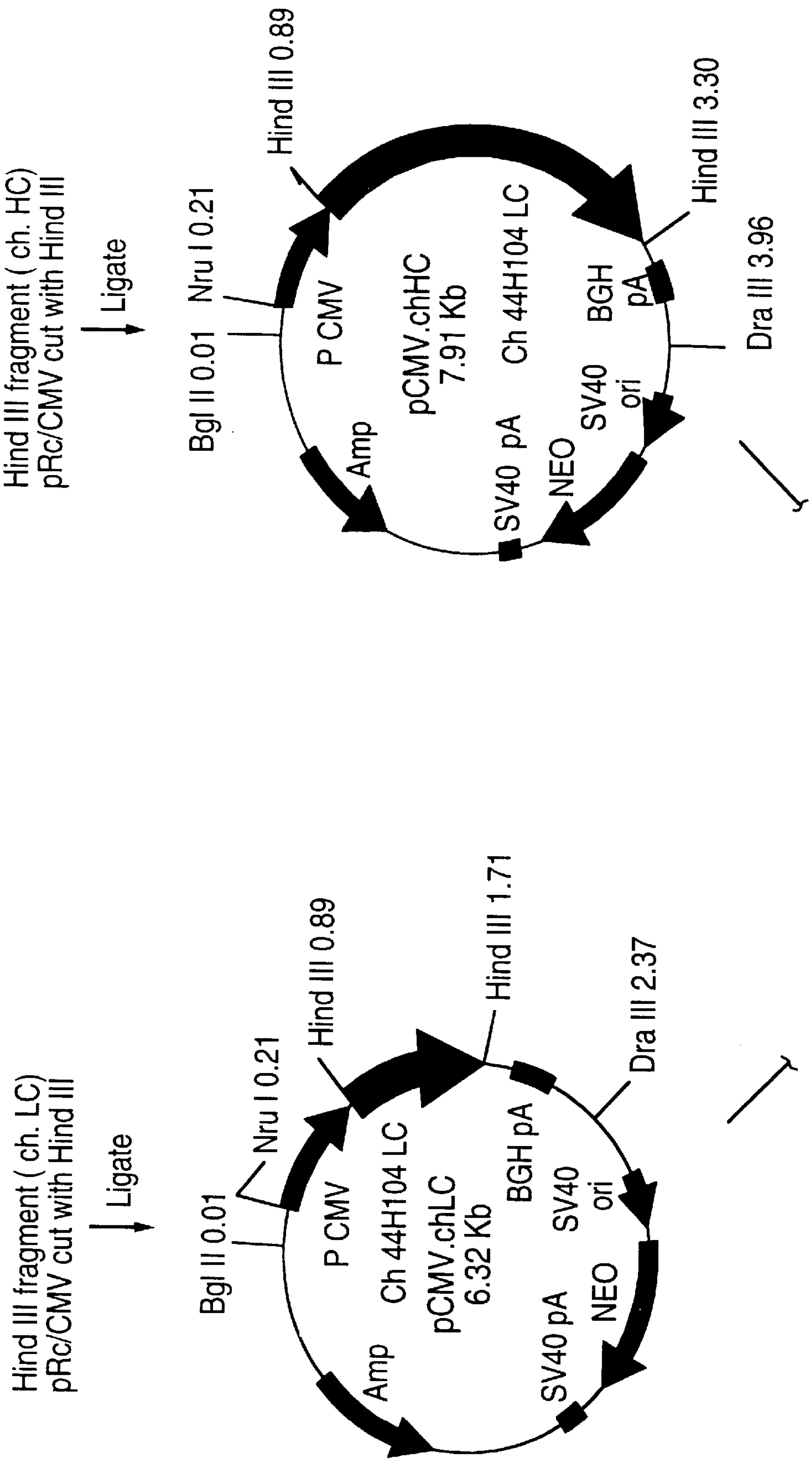
FIG. 5 contains the structures and schemes for construction of pRc/CMV based expression vectors for genes encoding chimeric light and heavy chain fusions with CLTB36. Plasmid pCMV·chLCHC is a tandem co-linear construction with both genes on the same vector. Plasmid pCMVdhfr·chLCHC is a co-linear plasmid with a murine dhfr encoding gene cassette.
Figure 5B:
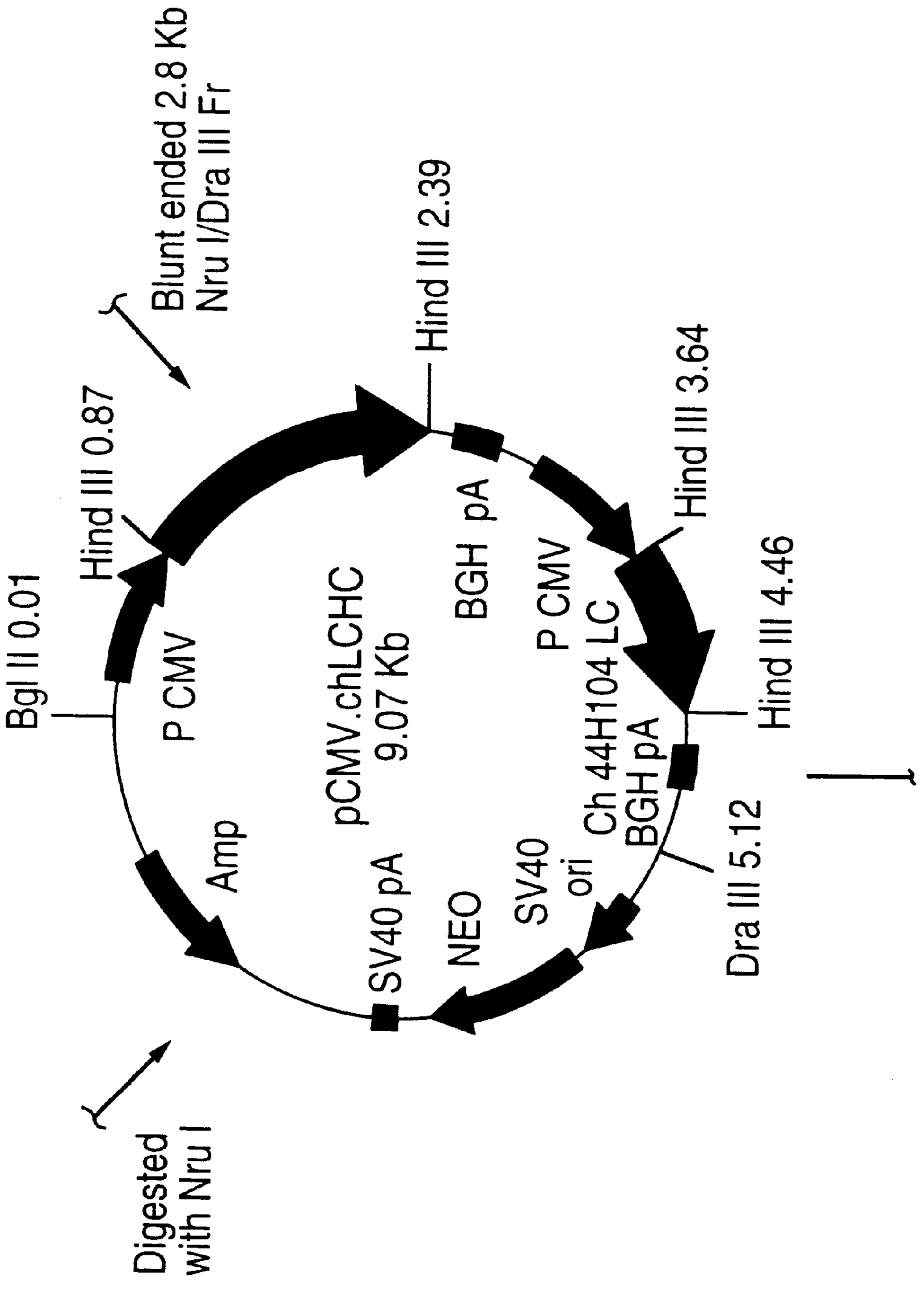
Figure 5C:
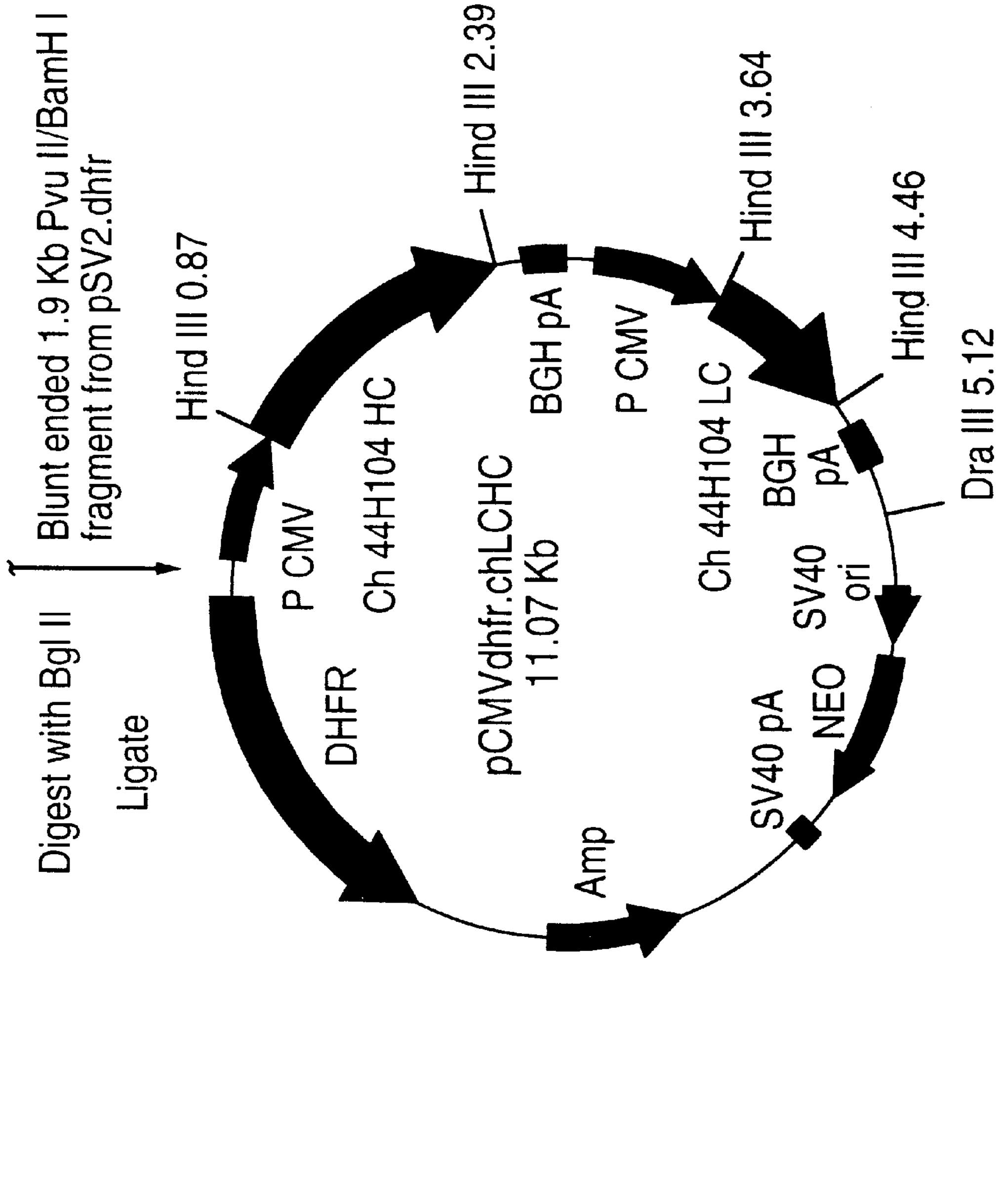

The PCRII vector containing $V_L$ gene insert was digested with a combination of Hind III and Xho I restriction endonucleases and the 400 bp insert isolated. Similarly polynucleotide fragments encoding the human Kappa gene and CLTB36 were excised out of pCRII cloning vectors using digestion with combinations of xho I/BamH I and BamH I/Hind III respectively. All three fragments were mixed (10–20 ng each) and ligated into an aliquot of Hind III digested expression plasmid pRC/CMV (Invitrogen) using standard protocols. The ligation reaction was used to transform competent *E. coli* TG1 cells and recombinants analyzed for inserts. The orientation of the insert was ascertained by restriction enzyme digest patterns and confirmed by DNA sequencing. This plasmid was designated as pCMV.chLC (FIG. 5).

Example 4

This Example illustrates assembly of a gene encoding the chimeric heavy chain of 44H104 mab conjugated with CTLB36.

Figure 4A:
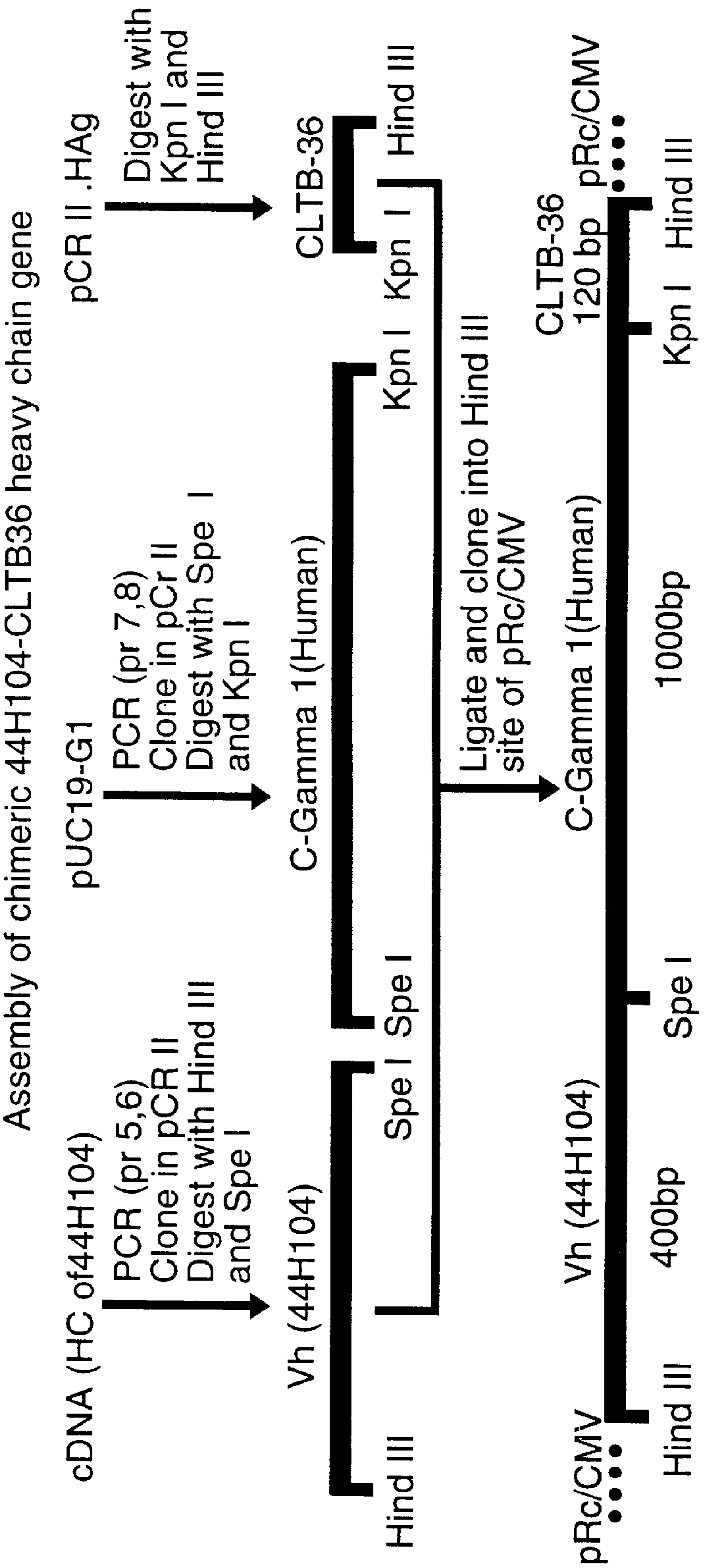
FIG. 4A shows a scheme for construction of chimeric 44H104 heavy chain gene using PCR-generated $V_H$ and $C_H$ DNA cassettes.

The gene for the chimeric heavy chain conjugated to CLTB36 was constructed from gene cassettes, generated in a manner similar to what has been described for the light It chain in Example 3. The detailed scheme and sequences of the oligonucleotide primers are shown in FIG. 4. Synthetic oligonucleotide primers 5 and 6 (SEQ ID Nos: 17, 18) were used in generating the $V_H$ gene from a plasmid template (pUC18) containing a cDNA insert encoding the heavy chain of mab 44H104. The primers were designed to incorporate a 5' Hind III restriction site, a kozak sequence and a silent mutation at the 3' ($V_H$–$C_H$ junction) resulting in a Spe I site for ligation to the constant domain gene. The PCR product was cloned into pCRII vector and the nucleotide sequence integrity of the insert confirmed. The human constant domain (C γ1) gene was obtained by the amplification of the insert encoding this in plasmid PUC19-G1 using PCR primers 7 and 8 (SEQ ID Nos: 19, 20). As with primers Pr. 5 and Pr. 6, the primers were designed to engineer a 5' Spe I site for ligation to the $V_H$ gene and a Kpn I recognition site fusion to the antigen gene. The PCR products were cloned into pCRII as before, and correct clones identified by DNA sequencing.

The gene cassettes encoding $V_H$, human Cγ1 and CLTB36 were obtained from sequences inserted into pRCII plasmid by digestion with combinations of Hind III/Spe I, Spe I/Kpn I and Kpn I/Hind III restriction enzymes respectively. The correct DNA fragments were isolated from agarose gels, mixed and ligated into Hind III digested pRC/CMV plasmid. These were used to transform competent *E. coli* cells and plasmid isolated from selected colonies. The plasmid was checked for inserts encoding the chimeric heavy chain-CLTB36 conjugate. The orientation of the gene with respect to the rest of the expression plasmid was established using restriction enzyme digestion patterns. The insert was also sequenced, the expression plasmid was designated pCMV.chHC (FIG. 5).

Example 5

This Example illustrates construction of expression plasmids.

The DNA sequences encoding the CLTB36 fusions with chimeric light and heavy chains were assembled in pRC/CMV (Invitrogen) to give plasmids pCMV.chLC and pCMV.chHC respectively (FIG. 5), as described in Examples 3 and 4. A single expression vector containing the genes for both light and heavy chains as distinct transcription units each under their own CMV promoter was constructed (the scheme is shown in FIG. 5). pCMV.chHC plasmid was digested with Nru I and Dra III and a 2.8 kb DNA fragment isolated on a 0.8 t agarose gel. The DNA fragment was blunt ended following a standard protocol (ref. 30) and using dNTP's and DNA polymerase (Klenow). The resulting DNA fragment was then ligated into plasmid pCMV.chLC linearized by digestion with Nru I restriction enzyme and the resulting co-linear vector designated as pCMV.chLCHC. The orientation and general structure of the plasmid is as shown in FIG. 5 and was confirmed by extensive restriction enzyme digestion analysis.

Expression plasmid pCMVdhfr.chLCHC was constructed by inserting a blunt ended 1.9 kb Pvu II/BamH I fragment from plasmid pSV2.dhfr (ref. 31), into the Bgl II restriction site of vector pCMV.chLCHC. This DNA fragment encodes a murine dihydrofolate reductase gene under the control of a SV40 promoter and terminating in a SV40 poly A. The orientation of the insert was confirmed by restriction digest analysis and is as shown for pCMVdhfr.chLCHC in FIG. 5. This plasmid was isolated from transformed TG1 cells by banding on cesium chloride (ref. 30) and used in transfection experiments.

Example 6

This Example illustrates the expression of chimeric 44H104-CLTB36 conjugates.

Initial expression was attempted by co-transfecting plasmids pCMV. chLC and pCMV.chHC prepared as described in Examples 3 and 4, into non-Ig secreting murine SP2/0 myeloma cells by electroporation. The SP2/0 cells were grown to mid log phase and then harvested; $1\times10^7$ cells were washed with cold PBS, centrifuged (4–5 ×g, for 5 min) and resuspended in 0.5 ml of PBS. Plasmid DNA linearized with Bgl II enzyme (10 μg of each plasmid) was added to the cell suspension and the mixture incubated on ice for 10 minutes. The suspension was transferred to a cold 0.4 cm electroporation cuvette and subjected to an electrical pulse at a setting of 700V and capacitance of 25 μF in a 'Gene Pulsar' electroporator (Biorad). The mixture was further incubated in ice (5 min.) and then left in supplemented RPMI (with 10% FBS) for 48 hours. Subsequently the cells were plated out in selective media consisting of RPMI medium supplemented with 10% FBS and 600 μg/ml of G418 (Sigma) in 96 well plates ($1\times10^4$ cells per well). The media was replaced every three days and after 2 weeks, wells displaying cell growth were checked for recombinant antibody secretion in supernatants by ELISA. Several pools/wells were selected and cloned by dilution cloning method (ref. 30) and again checked for ch. mab secretion. A few selected clones were expanded and stored as stocks with DMSO in liquid nitrogen. The expression plasmid pCMV.chLCHC was also used to transfect SP2/0 cells. The methodology of electroporation and establishment of cloned cell lines secreting chimeric mab-CLTB36 conjugates are as described above. The overall yield was, however, quite low.

The expression plasmid pCMVdhfr.chLCHC, prepared as described in Example 5, was transfected into YB2/0 rat myeloma cells (ATCC CRL 1662) following the protocols detailed by Shitara et al. (ref. 32). Essentially YB2/0 cells were grown in supplemented RPMI (containing 2 mM glutamine; penicillin 50 ug/ml and streptomycin 50 U/ml)

containing 10% FBS. Aliquots of $1\times10^7$ cells were collected, washed in PBS and taken up in 250 μl of PBS. These were mixed with non-linearized plasmid pCMVdhfr.chLCHC (10 μg) and electroporated at 200V, 250 μF capacitance in a Gene Pulsar electroporator (Bio Rad). The cells were then treated exactly like the electroporated SP2/0 cells described above and after 48 hours in non selective media were plated into ten 96-well plates in supplemented RPMI containing 600 μg/ml of G418. The media from wells displaying cell growth were analyzed for recombinant antibody and pools secreting the desired product identified. Some selected pools were transferred to 6 well plates and the media was replaced with supplemented RPMI containing 10% FBS, 600 μg/ml G418 and 50 nM of methotrexate (Sigma). The pools were adapted to this concentration of methotrexate (MTX) and then the level was increased to 100 nM. Subsequently the concentration of MTX was increased to 200 nM, then 500 nM, 1000 nM and finally 1500 nM. The cells were adapted to each of these levels through several passages and finally cloned by limiting dilution. Several clones secreting recombinant products from 3 to 30 μg/ml of spent culture medium (after protein A purification) were obtained and were used to obtain the chimeric mab in quantities large enough to permit experimentation in animals.

96 well microtitre plates (Maxisorp Immuno; Nunc) were coated with a Goat anti-human-kappa light chain ,It antibody fragment. The plates were washed in PBST (PBS containing 0.05% Tween 20), blocked with 0.1% casein in PBST, and incubated with aliquots (100 μl) of culture supernatants. A human myeloma IgG1K (Pharmingen) was used as a positive control. After washing, the plates were incubated with a goat anti-human IgG (Fc specific) $F(ab')_2$ conjugated to alkaline phosphatase. The un-bound conjugate was washed out and substrate pNPP (Gibco/BRL) was added to the wells in phosphotase buffer. After about 15 min and the colour development measured in a Dynatech MR5000 ELISA plate reader at a setting of 405–410 nm.

Example 7

This Example describes the isolation and purification of ch 44H104-CLTB36 conjugates.

Clones identified as high producers of conjugate in Example 6, exclusively from the pCMVdhfr.chLCHC transfection of YB2/0 cells and subsequent gene amplification experiments, were scaled up in supplemented RPMI containing G418 (600 μg/ml), methotrexate (1 μM) and 10% ultra low IgG FBS (from Gibco/BRL). The cells were allowed to grow in T-flasks until approximately half of them were dead (approximately 1 week). The culture was centrifuged and the supernatant collected. The spent media was stored at 4° C. with 0.1% sodium azide to prevent microbial growth.

The ch 44H104-CLTB36 conjugates in the supernatant were isolated by Protein A purification. The supernatant was passed through a Protein A-HyperD column (Sepracor). The column was washed and the bound material eluted with 0.2M glycine (pH 2.8); the fractions containing bound material were neutralized in 1.0M Tris (pH 8.0) and pooled. The fractions were dialyzed against PBS and finally concentrated on Amicon micro-concentrators. The protein content of the pooled, dialyzed and concentrated material was determined using a Standard Protein Assay Kit (Biorad Laboratories). The conjugate was stored at 4° C. in PBS.

To remove any high molecular weight aggregates, the Protein A purified material was further fractionated on a Sephacryl S-300 (HR; 9.5×90 cm) hplc column. The column was equilibrated with PBS and the sample applied in 2 ml aliquots. The column was run at a flow rate of 1 ml/min in PBS and the effluent monitored at 280 nm. The void volume peak (consisting of any aggregates) was collected separately from the peak corresponding to the non-aggregated material. The latter fractions were pooled and concentrated using a YM-10 ultra filtration membrane (Amicon).

Example 8

This Example describes characterization of ch mab 44H104-CLTB36 conjugate.

The conjugate produced following the procedure of Example 7 was assembled as a covalently linked dimer of heterodimers comprised of light and heavy chains. This was demonstrated by SDS/PAGE electrophoresis on 7.5 and 10% gels, running samples in non-reducing and reducing buffer respectively (see FIG. 9). The presence of CLTB36 peptide on the conjugates was determined by Western blotting using anti-CLTB36 guinea pig serum generated in house. The second antibody used in these experiments was a Goat anti-guinea pig IgG-alkaline phosphatase conjugate (Jackson Laboratories) (see FIG. 10).

Figure 8:
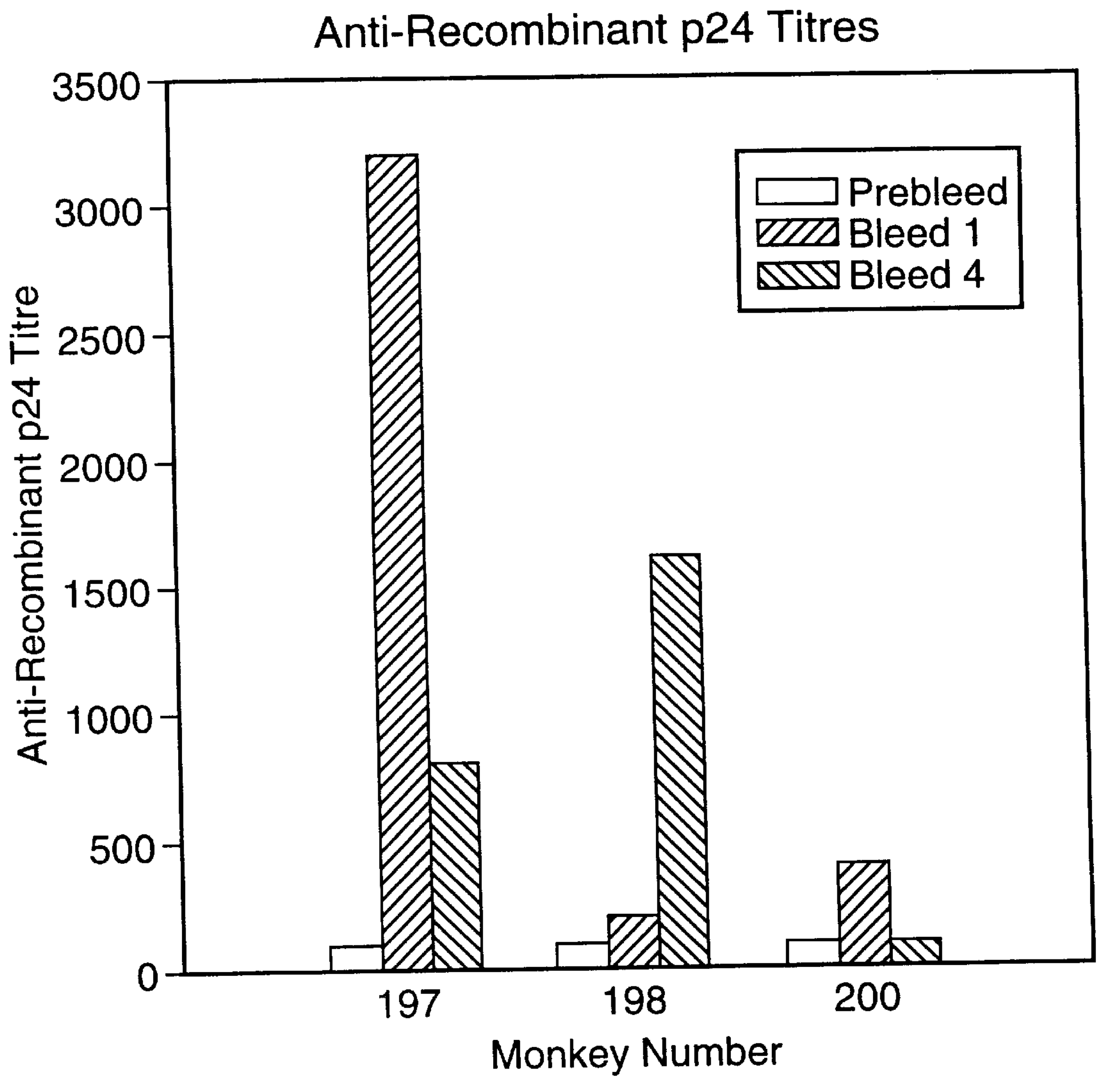
FIG. 8 illustrates anti-rP24 IgG titres in bleed 1 and 4 of macaques immunized with ch. 44H104-CLTB36 conjugates.

The conjugate was also analyzed for binding to class II molecules on HUT78 cells by Flow Cytometry using binding of recombinant conjugate to HUT78 cells. HUT78 cells (Human MHC class II expressing T cell lymphoma cells) were grown in supplemented RPMI containing 10% FBS. An aliquot of cells ($1\times10^6$ cells/tube) was distributed into 15 ml conical centrifuge tubes and washed with 2 ml of binding buffer (PBS containing 0.1% BSA and 0.1% $NaN_3$). The cells were collected after centrifugation (400×g for 5 min at 4° C.) and the pellet resuspended in binding buffer containing different concentrations of recombinant antibody conjugate (FIG. 8). The tubes were incubated on ice for 60 minutes with occasional shaking and then washed twice with chilled (4° C.) washing buffer (2 ml). The cells were suspended in 100 μl of a 1:20 dilution of fluoroscein isothiocyanate-conjugated goat anti-human IgG (Fc specific; Sigma Chemical Co.) and incubated further on ice for 30 minutes with occasional agitation. The cells were washed in binding buf fer(2×) and subsequently once in PBS containing 0.1% sodium azide ($NaN_3$). The cells were finally suspended in an aliquot of 1% paraformaldehyde in PBS (0.5 ml) and analyzed in the EPIC V flowcytometer (Coulter, Harpendon UK).

The recombinant conjugate was also analyzed for the presence of CLTB36 peptide by the same technique. For this analysis ,the anti-human conjugate in the above protocol was substituted with anti-CLTB36 guinea pig serum generated in house. This step was followed by 100 μl of 1:50 dilution of biotin-conjugated mouse IgG2b anti-guinea pig mab (sigma) for 30 minutes and finally with 100 μl of a 1:5 dilution of a streptavidin-phycoerythrin conjugate (Becton Dickinson; 30 min). Cells were washed as before and fixed with 1% paraformaldehyde in PBS and analyzed in the flowcytometer. Negative controls, consisting of cells treated as described above but without the incubation step with recombinant mab conjugate, were used in both assays.

Figure 6A:
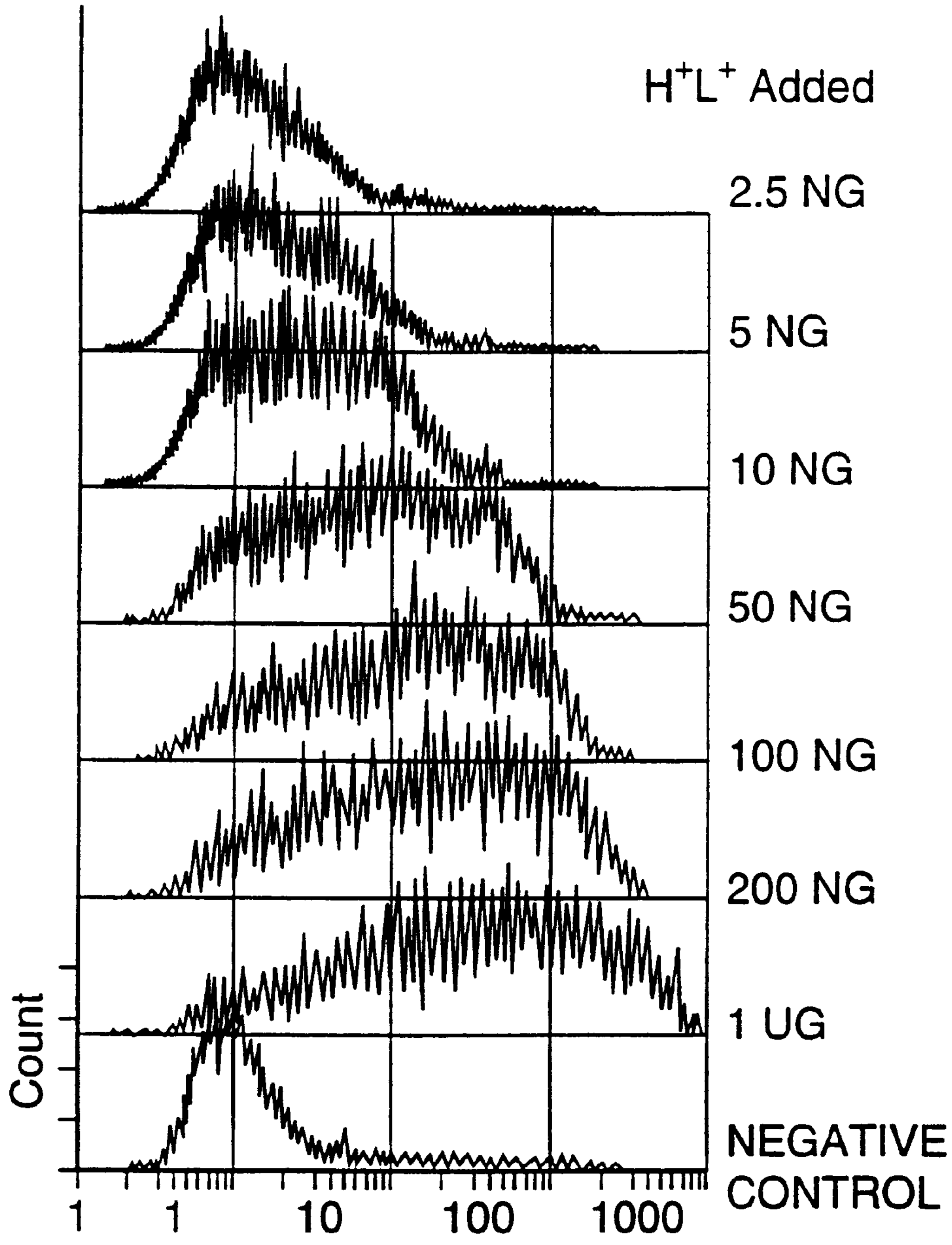
FIGS. 6A and 6B show flow cytometry data demonstrating binding of chimeric antibody conjugates to HUT78 cells. The conjugate is stained with a anti-human Fc specific antibody in panel A and anti-CLTB36 guinea pig serum in panel B.
Figure 6B:
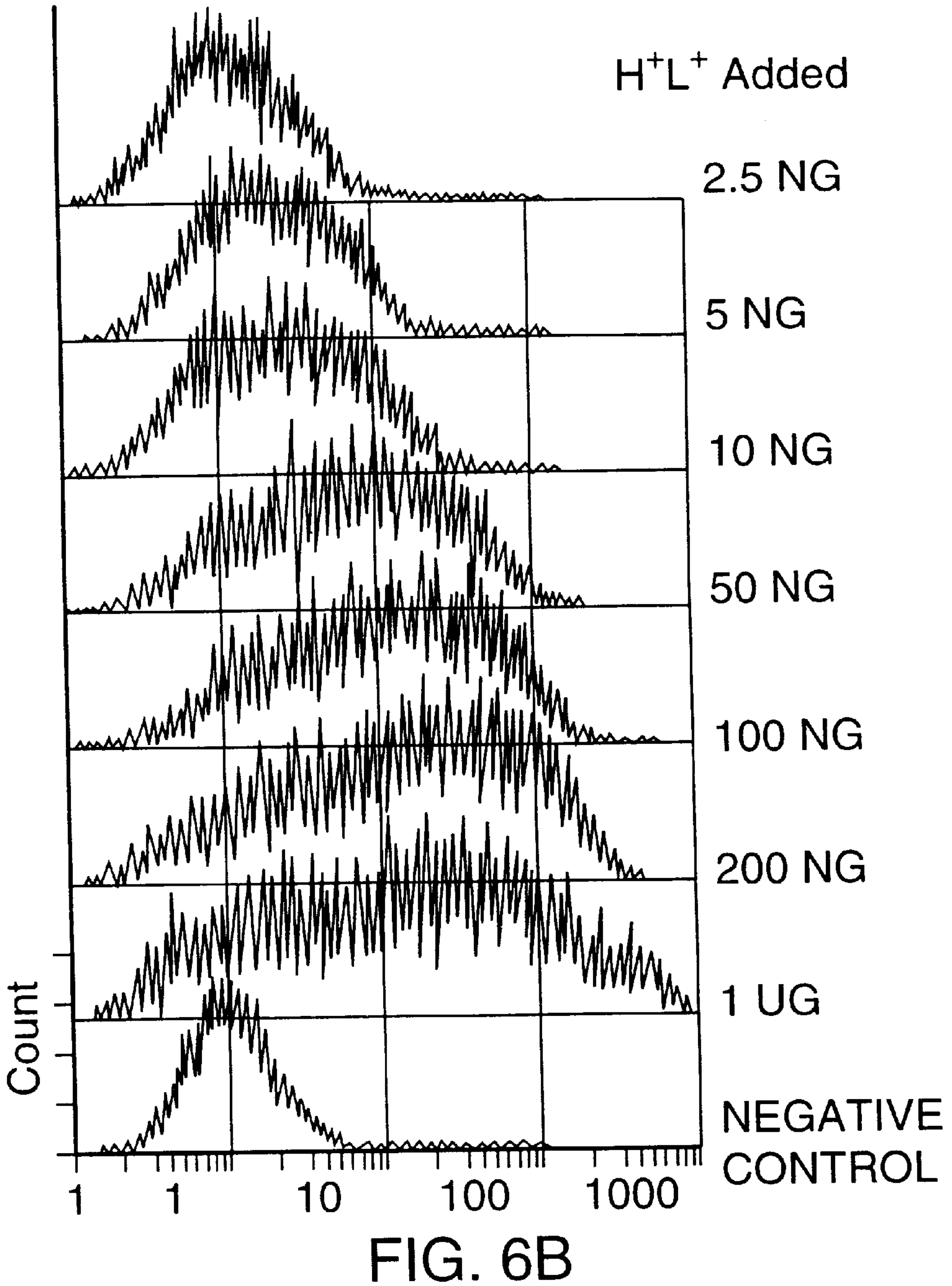

The results obtained are shown in FIG. 6. This analysis demonstrates the availability on the surface of cells of the peptide for binding to antibody.

Example 9

This Example describes immunization of macaques with ch 44H104-CLTB36 conjugates.

The immunogen (mab conjugate), prepared as in Example 7, was concentrated and filtered through a 0.22 μM filter. The protein concentration of this was estimated to be about 0.58 mg/ml in PBS.

Three cynomologous macaques were selected and serum samples from them these were screened for adventitious viral agents, such as SA8, HSV-1, HSV-2, V. Zoster, Chimp CMV, EBV, SRV-1, SRV-2, SRV-5, SIV, STLV-1, and B virus. The selected macaques (#197, 198 and 200) were bled and injected intramuscularly with 1.5 ml of PBS (containing 800 ug of protein, equivalent to 80 $\mu$g of peptide). The schedule set forth in the following Table 1 was established.

TABLE 1

| Week | Procedure |
|---|---|
| 0 | Pre-bleed<br>Primary injection<br>(0.8 mg of conjugate each) |
| 2 | Bleed 1 |
| 4 | Bleed 2 |
| 6 | Bleed 3<br>Boost 1<br>(0.8 $\mu$g of conjugate each) |
| 8 | Bleed 4<br>Bleed 5 |

The serum samples from the pre-bleed and Bleeds 1 to 5 were screened for anti-CLTB36 reactivity.

96 well microtitre plates (Polystyrene; Dynatech Labs) were coated with 10 $\mu$g/ml of CLTB36 in Carbonate-Bicarbonate buffer (0.05M; pH 9.6). The wells were blocked with 5% skim milk in PBS and subsequently washed in PBS-Tween 20 (0.05%). The serum samples were diluted serially (in 1% skim milk with 0.05% Tween 20) into the wells and incubated at 37° C. for 2 hours. The plates were washed and incubated with Goat anti-monkey IgG $F(ab')_2$ conjugated to Horse Radish Peroxidase (Cappel Laboratories). The excess conjugate was washed off and the colorimetric substrate TMB/$H_2O_2$ (ADI) added. The reaction was stopped after 5 min and absorbance measured at 450 and 540 nm in an ELISA Plate reader (EL 310; Biotech Instruments).

The protocol and reagents for an ELISA for P24 reactivity were as described for CLTB36 above; the difference being that the 96 well microtitre plates were coated with recombinant P24 (Dupont) at 1 $\mu$g/ml concentration in Carbonate-Bicarbonate buffer.

Figure 7:
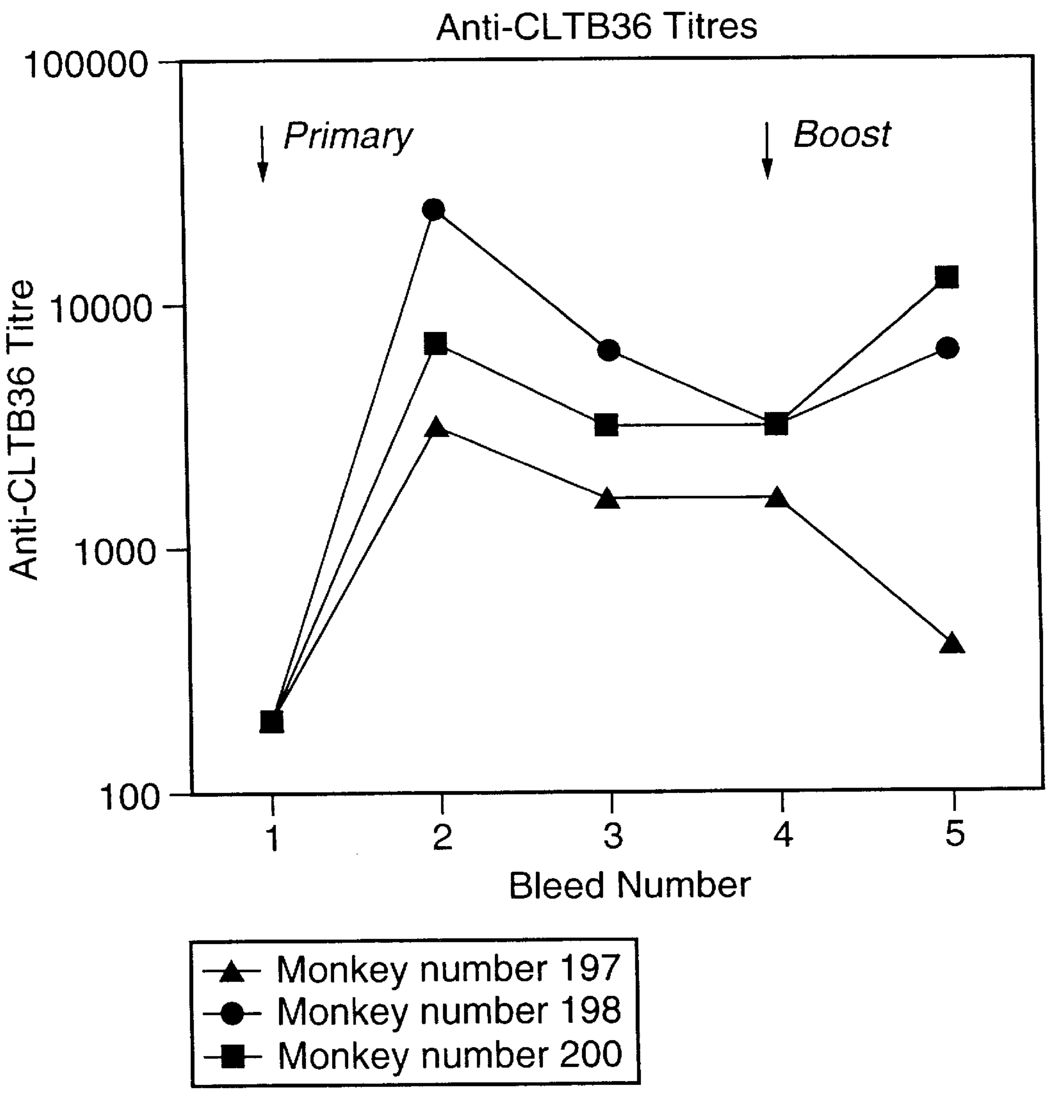
FIG. 7 illustrates anti-CLTB36 IgG titres in macaque sera as measured by ELISA, after immunization and boosting with ch·44H104-CLTB36 conjugates.

The IgG titres in different bleeds reactive against CLTB36 and measured by ELISA, are shown in FIG. 7. As may be seen, good priming responses were elicited by the recombinant targeting conjugate in PBS, in all three animals (up to about 1 in 25,000 in one animal). The observed ELISA titres diminish after 4 and 6 weeks and then increase again after a boosting dose of the immunogen. The boost in IgG titres was especially prominent in two animals out of the three, the third for unexplained reasons did not boost after such a promising primary response.

The pre-bleed monkey sera and Bleed 1 and 4 (2 weeks post priming and 2 weeks post boosting respectively) were also evaluated for IgG responses against recombinant P24 (CLTB36 has an epitope derived from this portion of HIV protein). Detectable P24 titres were measured in all three animals and are presented in FIG. 8.

A conjugate deficient in class II binding was constructed by mutating the $CDRH_3$ region of the heavy chain. This conjugate was injected into three cynomologous macaques as described above. Sera from the animals did not have any detectable CLTB36 specific antibodies, demonstrating that class II binding is responsible for the immunogenicity of ch 44H104-CLTB36 by selective delivery to antigen presenting cells.

SUMMARY OF DISCLOSURE

In summary of this disclosure, the present invention provides novel recombinantly-produced molecules containing an antigen moiety and a monoclonal antibody moiety, wherein the monoclonal antibody moiety is specific for a determinant expressed on antigen-presenting cells of a host, procedures for assembly of such molecules, nucleic acid molecules encoding such molecules and immunizing procedures using such molecules, whereby an enhanced immune response to the antigen moiety is achieved in the absence of adjuvants. Modifications are possible within the scope of this invention.

REFERENCES (1) Warren, H. S.; Vogel, F. R. and Chedid, L. A. A.; Ann. Rev. Immun. (1986) 4:369–388.
(2) Chapel, H. M. and Augus, P. J.; Clin. Exp. Immun. (1976) 24:538–541.
(3) Steward, M. W. and Howard, C. R.; Immun. Today, (1987) 8:51–58.
(4) Bittle, J. L.; Joughten, R. A.; Alexander, J.; Shinnick, T. M.; Sutcliffe, J.; Lerner, R. A.; Rowlands, D. J. and Brown, F.; Nature (Lond.) (1982) 298:30–33.
(5) Emmini, E. A.; Jameson, B. A. and Windmer, E.; Nature (Lond.) (1983) 304:699–703.
(6) Gerin, J. L.; Alexander, H.; Shih, J. W. -K.; Purcell, R. H.; Dapolito, G.; Engle, R.; Green, N.; Sutcliffe, J. G.; Shinnick, T. M. and Lerner, R. A.; Proc. Natn. Acad. Sci. U.S.A. (1983) 80:2365–2369.
(7) Gysin, J.; Barnwell, J.; Schlessinger, D. H.; Nussenzweig, V. and Nussenzweig, R. S.; J. exp. Med.; (1984) 160:935–940.
(8) Arnon, R. and Horwitz, R. J.; Curr. Biol. (1992) 4:449–453.
(9) Carayanniotis, G. and Barber, B. H.; Nature (Lond.) (1987) 327:59–61.
(10) Carayanniotis, G.; Vizi, E.; Parker, J. M. R.; Hodger, R. S. and Barber, B. H.; Mol. Immunol. (1988) 25:907–911.
(11) Skea, D. L.; Douglas, A. R.; Skehel, J. J. and Barber, B. H.; Vaccine (1993) 11:994–999.
(12) Carayanniotis, G.; Skea, D. L.; Luscher, M. A. and Barber, B. H.; Mol. Immunol. (1991) 28:261–267.
(13) Kawamura, H. and Berzofsky, J. A.; J. Immunol. (1986) 136:58–65.
(14) Snider, D. P. and Segal, D. M.; J. Immunol. (1987) 139:1609–1616.
(15) Snider, D. P. and Segal, D. M.; J. Immunol. (1989) 143:59–65.
(16) Casten, L. A.; Kawnaya, P. and Pierce, S. K.; J. Exp. Med. (1988) 168:171–180.
(17) Casten, L. A. and Pierce, S. K.; J. Immunol. (1988) 140:404–410.
(18) Sollazo, M.; Billetta, R. and Zanetti, M.; Protein Eng. (1990) 4:215–220.
(19) Billetta, R.; Hollingdale, R. M. and Zanetti, M.; Proc. Natl. Acad. Sci. (USA) (1991) 83:4713–4717.
(20) Zanetti, M.; Nature (Lond.), (1992) 355:476–477.
(21) Zaghouani, H.; Krystal, M.; Kuzu, H.; Moran, T.; Shah, H.; Kuzu, Y.; Schulman, J. and Bona, C.; J. Immunol. (1992) 148:3604–3609.
(22) Zaghouani, H.; Steinman, R.; Nonacs, R.; Shah, H.; Gerhard, W. and Bona, C.; Science (1993) 259:224–227.
(23) Brumeanu, T.; Swiggard, W. J.; Steinman, R. M.; Bona, C. A. and Zaghouani, H.; J. Exp. Med. (1993) 178:1795–1799.

(24) Zaghouani, H.; Anderson, S. A.; Sperber, K. E.; Daian, C.; Kennedy, R. C.; Mayer, L. and Bona, C. A.; Proc. Natl. Acad. Sci. (USA), (1995) 92:631–635.

(25) Quackenbush, E. and Letarte, M.; J. Immunol. (1985) 134:1276–1285.

(26) Dubiski, S.; Cinader, B.; Chou, C. -T.; Carpentier, L. and Letarte, M.; Mol. Immunol. (1988) 25:713–718.

(27) Baier, G.; Baier-Bitterlich, G.; Looney, D. J. and Altman, A.; J. Virology (1995) 69:2357–2365.

(28) Orlandi, R.; Güssow, D. H.; Jones, P. T. and Winter, G.; Proc. Nat'l. Acad. Sci. (USA), (1989) 86:3833–3837.

(29) "Molecular Cloning: A Laboratory Manual", ed. Sambrook, J.; Fritsch, E. F. and Maniatis, T.; (1989) Cold Spring Harbour Laboratory Press.

(30) Kozak, M.; Cell, (1986), 44:283–288.

(31) Subramani, S.; Mulligan, R. and Berg, P.; Mol. Cell. Biol., (1981), 1:854–864.

(32) Shitara, K.; Nakamura, K.; Tokutake-Tanaka, Y.; Fukushima, M. and Hanai, N.; Jour. of Immunol. Meth., (1994), 167:271–278.

(33) Ulmer et al. 1993, Curre. Opinion. Invest. Drugs 2:983–989.

---

What we claim is:

1. A method of generating an immune response in a host, comprising:

administering thereto an immuno-effective amount of an immunogenic composition comprising a recombinant conjugate antibody molecule, consisting of a bivalent monoclonal antibody moiety having the entire heavy and light chains and specific for a surface structure of antigen presenting cells, said monoclonal antibody moiety being genetically modified to contain at least one antigen moiety, each said antigen moiety being located exclusively at a preselected site on said monoclonal antibody moiety, whereby said conjugate antibody molecule is capable of delivering said antigen moiety to the antigen presenting cells of a host and capable of eliciting an immune response to said antigen moiety in the host.

2. The method of claim 1 wherein said antigen presenting cells are selected from the group consisting of class I major histocompatibility expressing cells, class II major histocompatibility expressing cells, dendritic cells and $CD4^+$ cells.

3.The method of claim 1 wherein said at least one antigen moiety is located at at least one end of at least one of the heavy and light chains of said monoclonal antibody moiety.

4. The method of claim 3 wherein said at least one antigen moiety is located at the C-terminal end of said at least one of the heavy and light chains of said monoclonal antibody moiety.

5. The method of claim 4 wherein said at least on antigen moiety is located at the C-terminal end of both said heavy and light chains of said monoclonal antibody moiety.

6. The method of claim 5 wherein said at least one antigen moiety is directly linked to the C-terminal end of both said heavy and light chains of said monoclonal antiobody moiety.

7. The method of claim 6 wherein said at least one antigen moiety is an inherently weakly-immunogenic antigen moiety.

8. The method of claim 6 wherein said monoclonal antibody moiety is genetically modified to contain a plurality of antigen moieties.

9. The method of claim 8 wherein said plurality of antigen moieties is plurality of a single antigen moiety.

10. The method of claim 8 wherein said plurality of antigen moieties is a plurality of different antigenic moieties.

11. The method of claim 7 wherein said at least one antigen moiety is a peptide having from 6 to 100 amino acids and containing at least one epitope.

* * * * *